(12) United States Patent
Kockro

(10) Patent No.: US 7,491,198 B2
(45) Date of Patent: Feb. 17, 2009

(54) COMPUTER ENHANCED SURGICAL NAVIGATION IMAGING SYSTEM (CAMERA PROBE)

(75) Inventor: Ralf Alfons Kockro, Singapore (SG)

(73) Assignee: Bracco Imaging S.p.A., Milan (IT)

( * ) Notice: Subject to any disclaimer, the term of this patent is extended or adjusted under 35 U.S.C. 154(b) by 0 days.

(21) Appl. No.: 10/832,902

(22) Filed: Apr. 27, 2004

(65) Prior Publication Data
US 2005/0015005 A1    Jan. 20, 2005

(51) Int. Cl.
*A61B 17/00* (2006.01)
(52) U.S. Cl. .................... 606/1; 600/117; 600/118; 600/424; 600/427; 600/429; 606/130
(58) Field of Classification Search .................. None
See application file for complete search history.

(56) References Cited

U.S. PATENT DOCUMENTS 6,036,637 A * 3/2000 Kudo ................... 600/173
6,167,296 A * 12/2000 Shahidi ................ 600/427
6,535,756 B1 * 3/2003 Simon et al. ........... 600/424

* cited by examiner

*Primary Examiner*—Linda C Dvorak
*Assistant Examiner*—Matthew J Kasztejna
(74) *Attorney, Agent, or Firm*—Aaron S. Haleva; Kramer Levin Naftalis & Frankel, LLP

(57) ABSTRACT

A system and method for navigation within a surgical field are presented. In exemplary embodiments according to the present invention a micro-camera can be provided in a handheld navigation probe tracked by a tracking system. This enables navigation within an operative scene by viewing real-time images from the viewpoint of the micro-camera within the navigation probe, which are overlaid with computer generated 3D graphics depicting structures of interest generated from pre-operative scans. Various transparency settings of the camera image and the superimposed 3D graphics can enhance the depth perception, and distances between a tip of the probe and any of the superimposed 3D structures along a virtual ray extending from the probe tip can be dynamically displayed in the combined image. In exemplary embodiments of the invention a virtual interface can be displayed adjacent to the combined image on a system display, thus facilitating interaction with various navigation related functions. In exemplary embodiments according to the present invention virtual reality systems can be used to plan surgical approaches with multi-modal CT and MRI data. This allows for generating 3D structures as well as marking ideal surgical paths. The system and method presented thus enable transfer of a surgical planning scenario to a real-time view of an actual surgical field, thus enhancing navigation.

15 Claims, 31 Drawing Sheets
(26 of 31 Drawing Sheet(s) Filed in Color)

Corresponding view from the Camera-Probe
Showing cube (seen from video) and
Cylinder (overlaid from computer generated imagery)

Figure 16: Data Flow in Pre-operative Planning

Figure 17: Registration Process

Figure 18: Data Flow in Intra-Operative Navigation

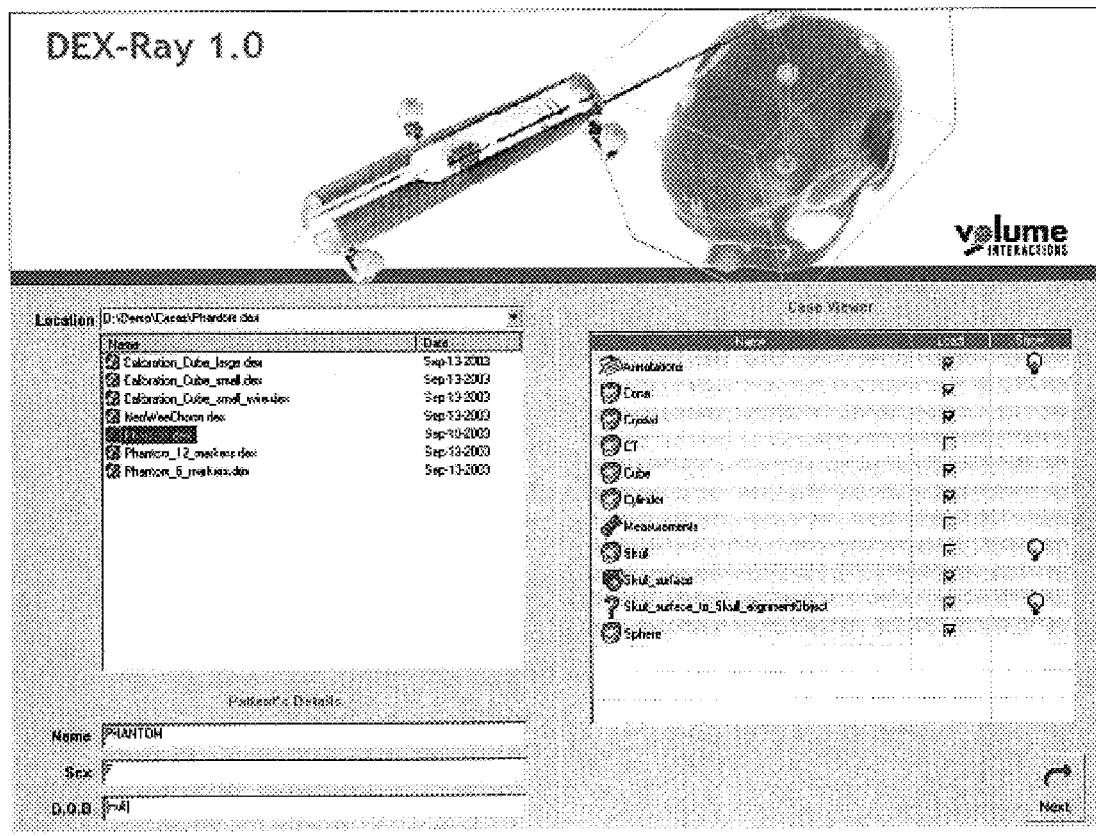
Figure 25  Data loaded

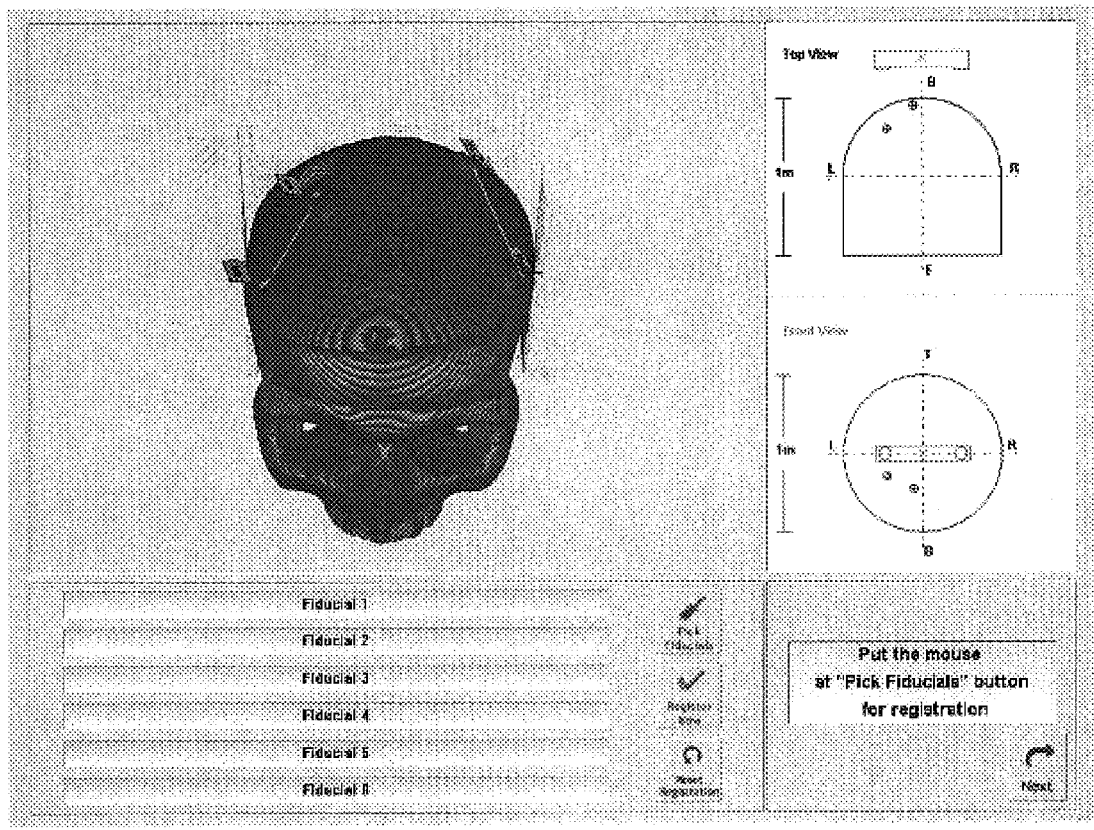
Figure 26 Pre-registration

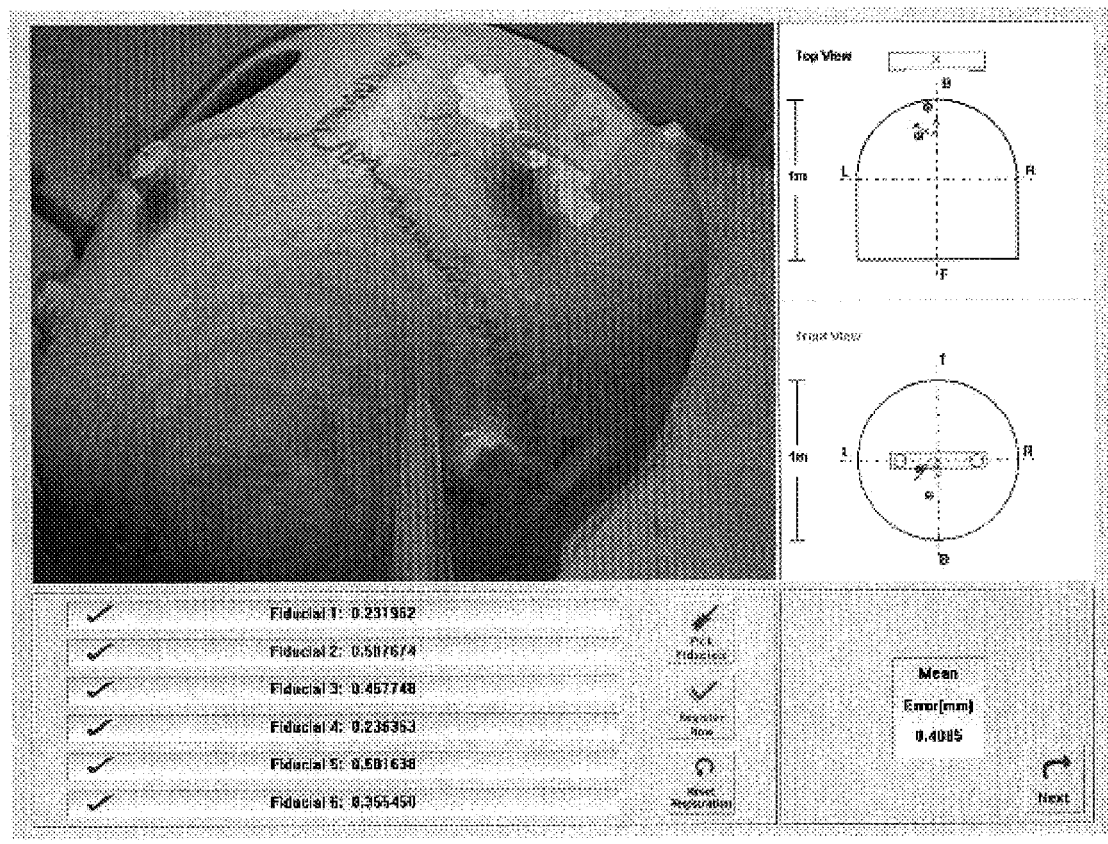
Figure 27  Post-registration

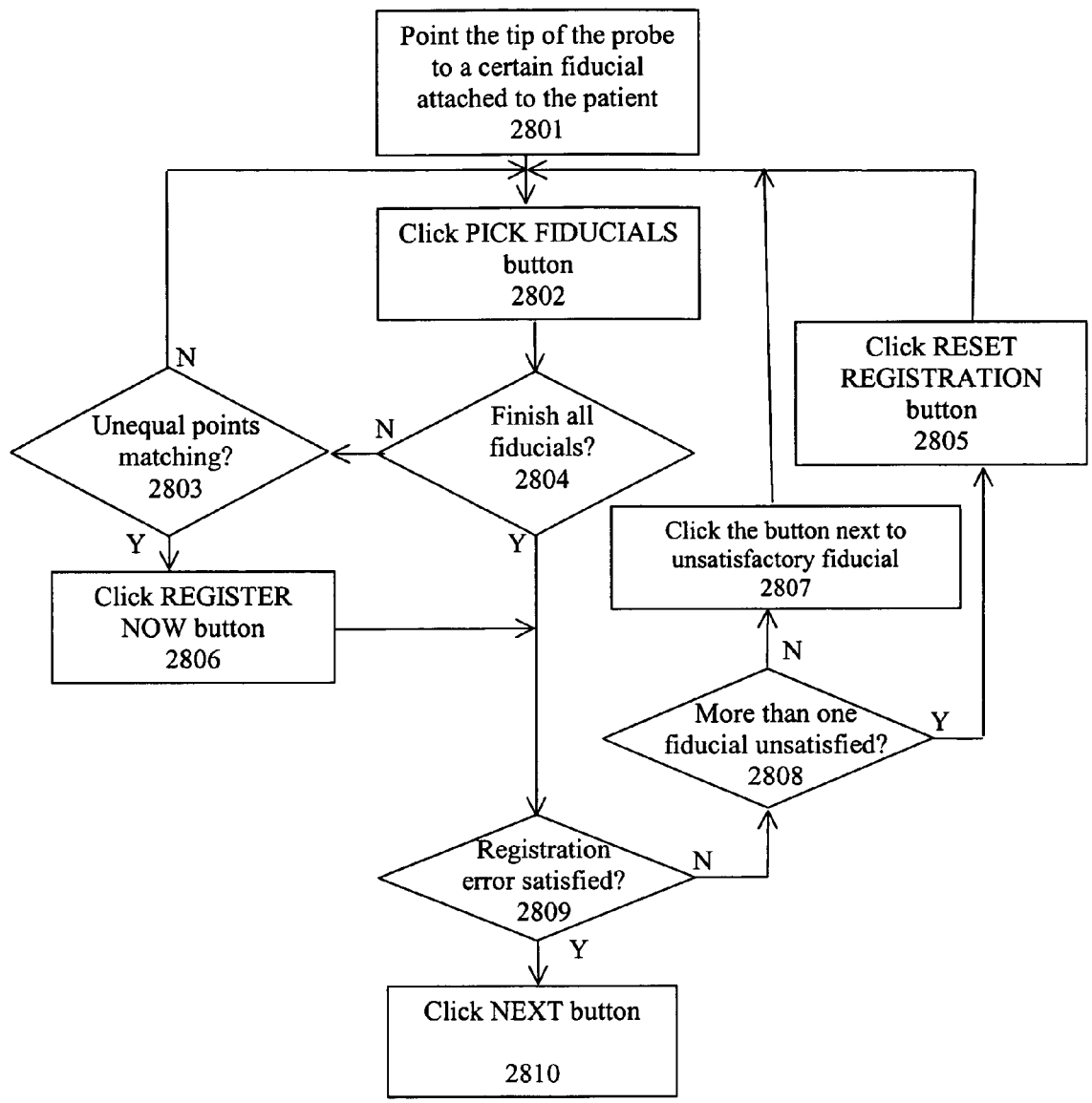
Fig. 28 – Registration Process Flow

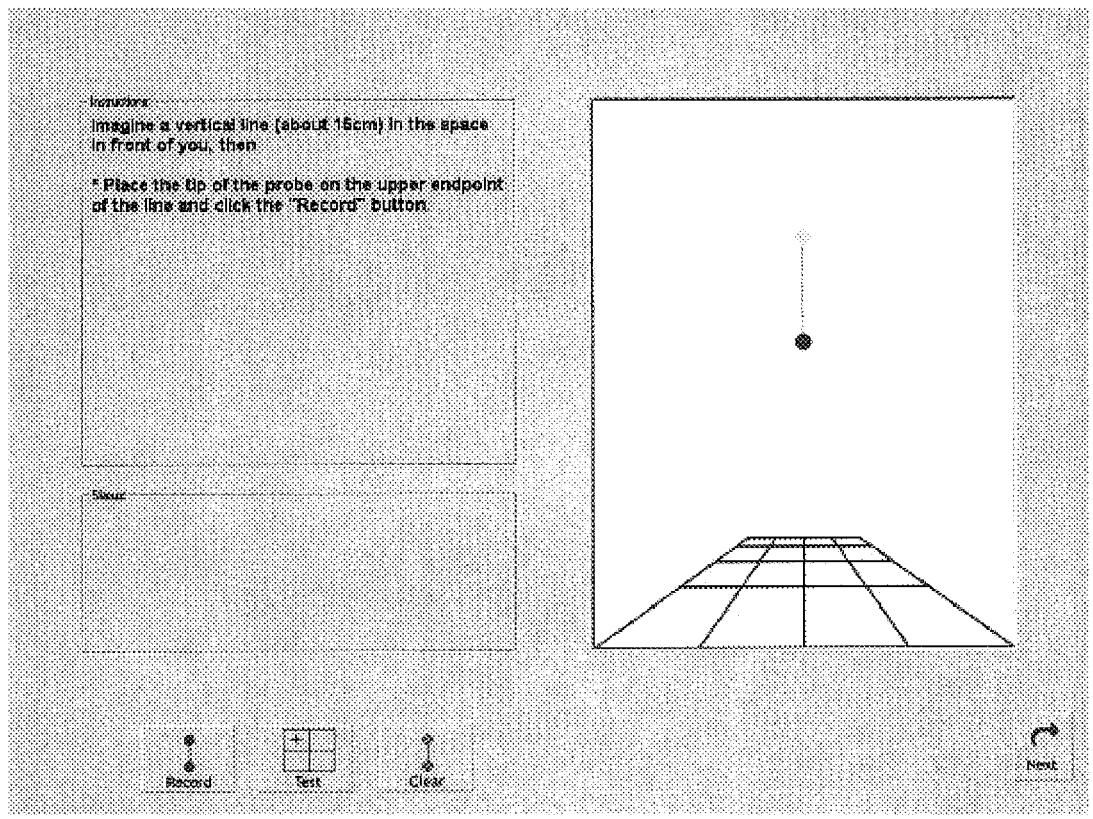
Figure 29 - Interface of vector recording page

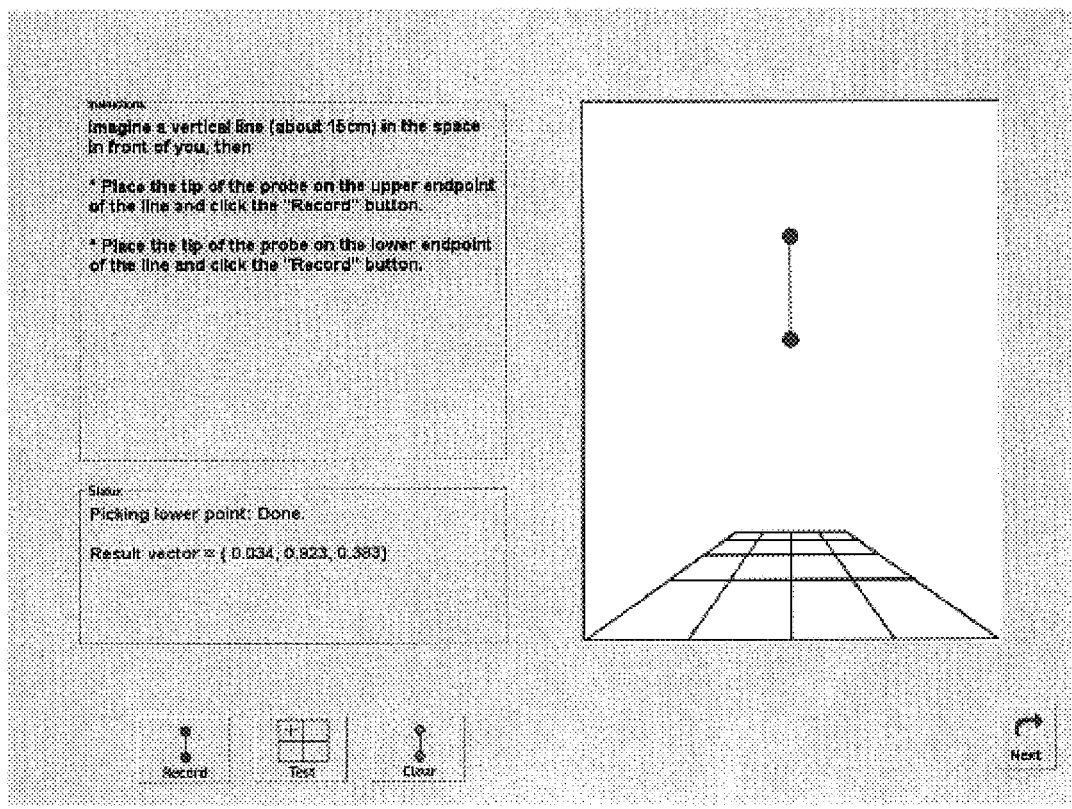
Figure 30 - Running status box

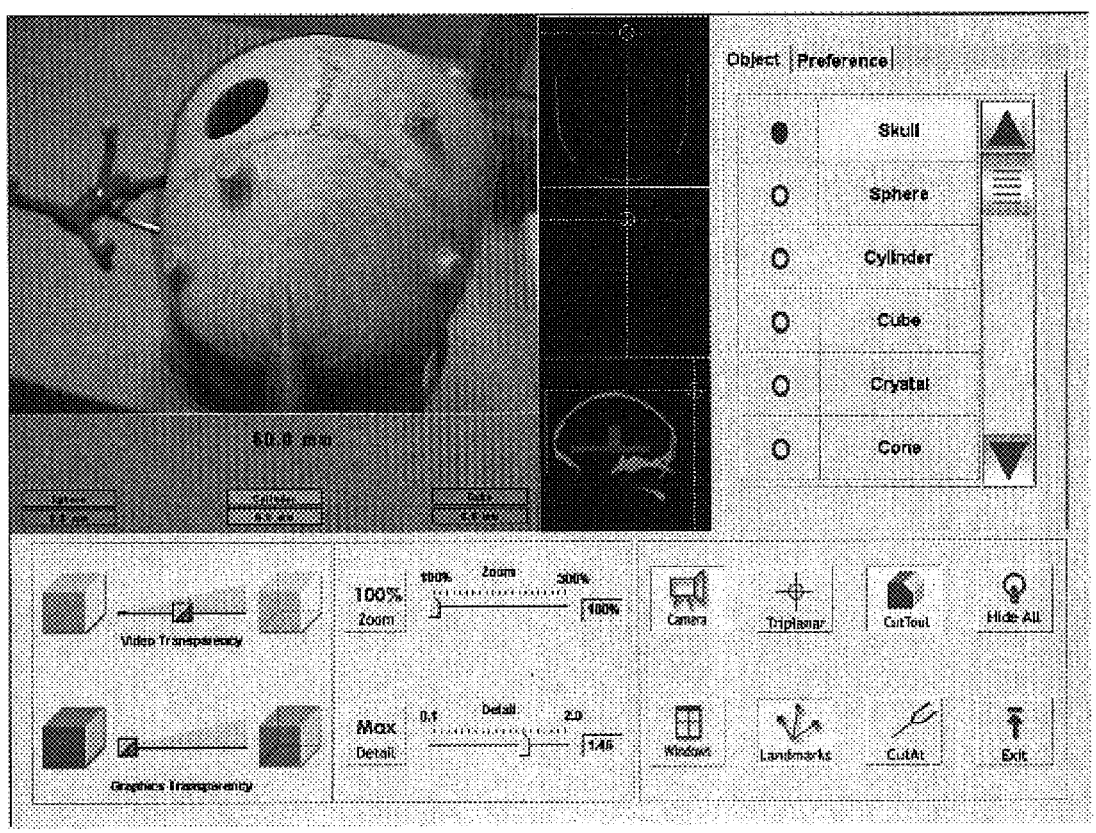
Figure 31 - Console mode

COMPUTER ENHANCED SURGICAL NAVIGATION IMAGING SYSTEM (CAMERA PROBE)

FIELD OF THE INVENTION

The present invention relates to computer assisted surgery, and more particularly to a computer enhanced surgical navigation imaging system. The invention further relates to methods and devices for operation and control of such system.

BACKGROUND OF THE INVENTION

Image guidance systems are becoming more common and widely adapted in neurosurgery. Such systems have been proven to increase the accuracy and reduce the invasiveness of a wide range of surgical procedures. Currently, image guided surgical systems ("Navigation Systems") are based on obtaining a pre-operative series of imaging data, such as, e.g., MRI and CT which are registered to the patient in the physical world by means of an optical tracking system. Such optical tracking allows for detecting markers placed on a patient's skin (known as "fiducials") and correlating them with their counterparts within such pre-operation imaging data.

In many conventional image guided operations, images generated from pre-operative scan data are displayed as two dimensional images in three orthogonal planes through the image volume, while a surgeon holds a probe that is tracked by a tracking system. When such a probe is introduced into a surgical field, the position of its tip is represented as an icon drawn on the images. By linking the preoperative imaging data with the actual surgical field, navigation systems can provide a surgeon (or other practitioner) with valuable information, i.e., the exact localization of a tool in relation to surrounding structures within the patient's body. This helps to relate the actual tissues of an intra-operative field to their images used in pre-operative planning.

However, in such systems the displayed images are only two dimensional, and to be fully utilized must be mentally reconciled into a three dimensional image in the surgeon's mind. Thus, sharing a problem which is common to all conventional navigation systems which present imaging data in 2D orthogonal slices, a surgeon has to make a significant mental effort to relate the spatial orientation of a pre-operative image series (displayed, for example, in separate axial, coronal, and sagittal planes) to the physical orientation of the patient's area of interest, such as, for example, a patient's head in a neurosurgical procedure which is often mostly covered by draping during the operative procedure. Other conventional systems display a three dimensional ("3D") data set in a fourth display window. However, in such systems the displayed 3D view is merely a 3D rendering of pre-operative scan data and is not at all correlated to or merged with the surgeon's actual view of the surgical field. Thus, while using such systems, a surgeon is still forced to mentally reconcile the displayed 3D view with his real time view of the actual surgical field he or she is working in. This requires the cumbersome task of the surgeon continually switching his or her view between the 3D rendering of the object of interest (usually presented as an "abstract" object against a black background) and the actual surgical field. What is needed in the art is a less cumbersome method of presenting preoperative data to a surgeon during surgery so as to enhance his or her real time surgical navigation capabilities.

SUMMARY OF THE INVENTION

A system and method for computer enhanced surgical navigation are presented. In an exemplary embodiment according to the present invention a micro camera can be provided in a hand-held navigation probe which can be tracked by a tracking system. This enables navigation within a given operative field by viewing real-time images acquired by the micro-camera which are overlaid with computer generated 3D graphics depicting structures of interest. Various transparency settings of the real-time images and the superimposed 3D graphics can enhance depth perception, and distances between the probe and superimposed 3D graphical "objects" can be dynamically displayed in the combined image. In exemplary embodiments of the invention a virtual interface can also be displayed, adjacent to the combined image on a system display, facilitating interaction with various navigation related and display functions. In exemplary embodiments of the present invention virtual reality systems can be used to plan surgical approaches with multi-modal CT and MRI data acquired pre-operatively. This allows for the generation of 3D structures as well as the marking of ideal surgical paths. The system and method presented thus enable transfer of a surgical planning scenario into real-time images of an actual surgical field.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 25 depicts an exemplary screen shot of a data loading page after patient data has been loaded in an exemplary embodiment of the present invention;

FIG. 26 depicts an exemplary screen shot of an exemplary registration interface according to the exemplary embodiment of the present invention depicted in FIG. 25;

FIG. 27 depicts the exemplary registration interface of FIG. 26 after registration has been accomplished;

FIG. 28 depicts an exemplary process flow chart for the exemplary registration operation depicted in FIGS. 26-27;

FIGS. 29 and 30 depict two stages of an exemplary vector definition operation according to the exemplary embodiment of the present invention depicted in FIG. 25; and FIG. 31 depicts an exemplary screen shot of operation of the exemplary DEX-Ray system navigation page in console mode according to the exemplary embodiment of the present invention shown in FIG. 25.

The patent or application file contains at least one drawing executed in color. Copies of this patent or patent application publication with color drawings will be provided by the U.S. Patent Office upon request and payment of the necessary fee.

DETAILED DESCRIPTION OF THE INVENTION

A novel system and method for surgical navigation are presented. In an exemplary embodiment according to the present invention 3D representations of pre-operative imaging data are overlayed on real-time video of a surgical scene, simultaneously providing a surgeon or other user the ability to navigate within a surgical field by displaying (in addition to the real-time video images) axial, coronal and sagittal planes of scan data at a current point of interest. In exemplary embodiments according to the present invention this functionality is achieved by combining a tracked micro video camera with a computer imaging system. In such exemplary embodiments a computer imaging system can display real-time video images acquired by the camera overlaid with computer generated images rendered from data acquired pre-operatively.

Figure 1:
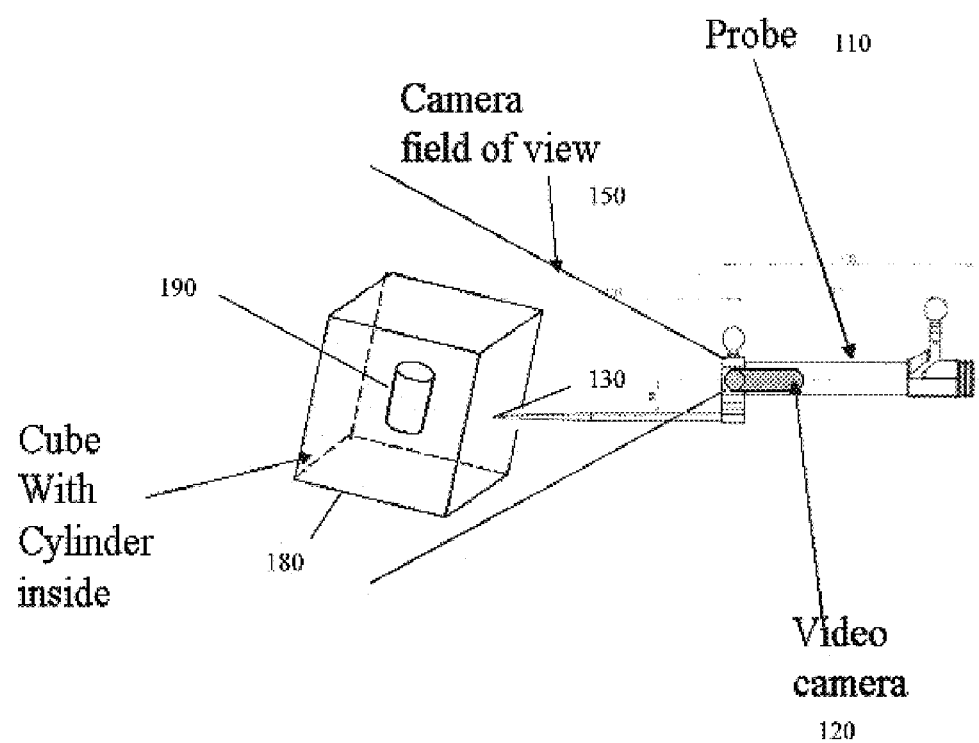
FIG. 1 depicts an exemplary probe whose tip is near a real object with a computer generated virtual object shown as being inside the real object according to an exemplary embodiment of the present invention.

With reference to FIG. 1, an example probe 110 according to an exemplary embodiment of the present invention is shown. The probe 110 contains a video camera 120, and pointer 130 is attached to its front end. In an exemplary embodiment according to the present invention, camera 120 can be mounted such that the tip of the probe is visible within the camera's field of view 150. Thus, a surgeon can, for example, look solely at a system display monitor throughout a surgical procedure, see the actual video image as well as any selected computer generated objects, and need not continually shift his view from the field of surgery to a display monitor. The camera's weight can be, for example, very light and thus the camera can easily be hand-held. A pointer 130 can be used to point to a region or object of interest, such as, for example, cube 180. If the object is opaque, there may be other objects of interest within its interior, such as, for example, cylinder 190. While the real-time video cannot display the cylinder 190 due to the opacity of the cube 180, the computer imaging system can, thus affording a user an augmented and enhanced view of a region of interest.

As described more fully below, in exemplary embodiments according to the present invention computer generated 3D representations of preoperative imaging data (including, for example, surgical plan data and selected objects and structures of interest) can be displayed in a semitransparent mode over the real time video. At the same time, axial, coronal and sagittal image planes containing pre-operative scan data of the region of interest can also be displayed in three separate windows. As described below, such image planes can be, for example, dynamically varying as to content based upon the then current position of pointer tip 130 of probe 110.

Figure 2:
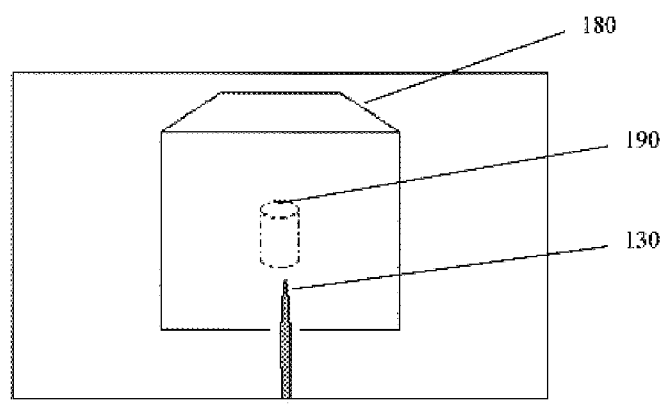
FIG. 2 depicts an exemplary display of the scene depicted in FIG. 1 from the camera's viewpoint according to an exemplary embodiment of the present invention.

FIG. 2 depicts the exemplary scene of FIG. 1 from the point of view of camera 120. In an augmented imaging system according to an exemplary embodiment of the present invention, both the cube 180 (from real-time video) and the computer generated cylinder 190 which lurks within it (generated form pre-operative scan data) are visible. In an actual surgical procedure, for example, it may be crucial to know the exact location of a known invisible or occluded object relative to a visible one within the surgical field. For example, when operating subcranially to remove a visible tumor behind which lurks an important structure which must not be touched, such as, for example, the optic nerve, it is crucial to know the exact location of the optic nerve relative to the tumor. With reference to FIG. 2, cylinder 190 is an exemplary representation of such an invisible object whose precise distance from a probe tip 130 when held near a visible object (represented here by cube 180) is critical to a user.

The system, methods and apparatus of the present invention thus enable a user to see "beyond the normal field of view" before and during a procedure, such as, for example, by visualizing the position of a tumor or proximate blood vessels by looking onto and beyond the tip of a pointer 130 (with reference to FIGS. 1-2). Additionally, as described below in connection with FIGS. 19-24, the system can, for example, display distances along the direction of the pointer tip to any structures which are "beyond the field of view" (and thus invisible to the camera or naked eye). These distances can, for example, be displayed in numerical or other readout formats, thus allowing a user, based upon pre-operative data stored in the system, to see the changing distance from a probe tip to a structure of interest (known to exist from pre-operative scan data) as he or she moves the probe. This allows a user to always be aware just how near he is to highly sensitive or important hidden structures.

Given the system, methods and apparatus of the present invention, a novel method of surgical or other intra-body navigation becomes possible. In exemplary embodiments according to the present invention, combined navigation by means of (a) a real-time view of the surgical field as augmented by a computer generated display of 3D pre-operative patient data, and (b) a simultaneous display of dynamically changing axial, coronal and sagittal images (rendered from pre operative scans) with the real time location of a pointer tip as the cross-section point, is provided. Since all image windows can be, for example, displayed on one monitor, the information provided in these two display modes is mutually enhancing. This can, for example, result in better spatial understanding by a user, making navigation easier and more comprehensive.

The 3D data presented in a navigation system according to an exemplary embodiment of the present invention can, for example, be generated by a 3D volume rendering system, such as, for example, the VizDexter™ 3D image visualization system developed by Volume Interactions Pte Ltd of Singapore, or the RadioDexter™ system by the same company. The VizDexter™ and RadioDexter™ systems each allow for working with multimodal (e.g., fused CT and MRI) images in a virtual reality environment of a three-dimensional data display system. In exemplary embodiments according to the present invention, such a three-dimensional data display system can be, for example, the Dextroscope™, also provided by Volume Interactions Pte Ltd.

Apparatus Detail

Figure 5:
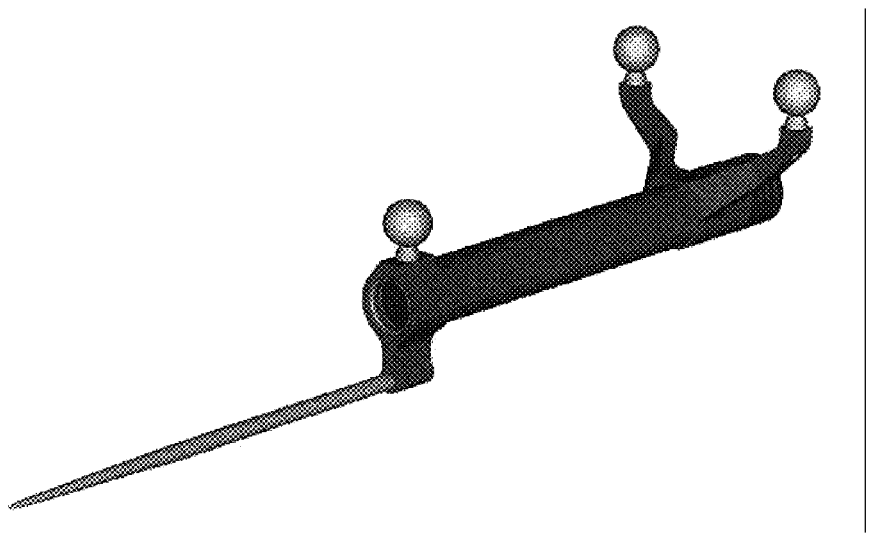
FIG. 5 is a schematic drawing of an example probe according to an exemplary embodiment of the present invention.
Figure 6:
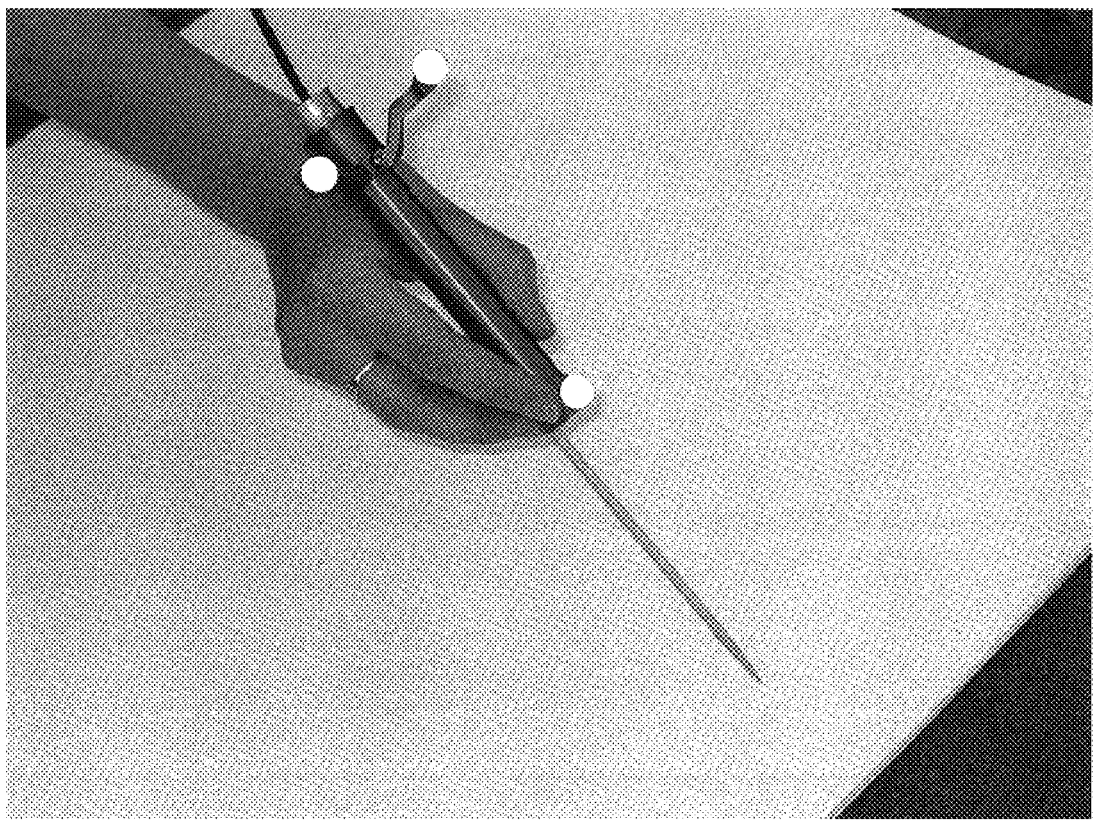
FIG. 6 depicts the exemplary probe of FIG. 3 held in a user's right hand shown from a different angle.
Figure 7:
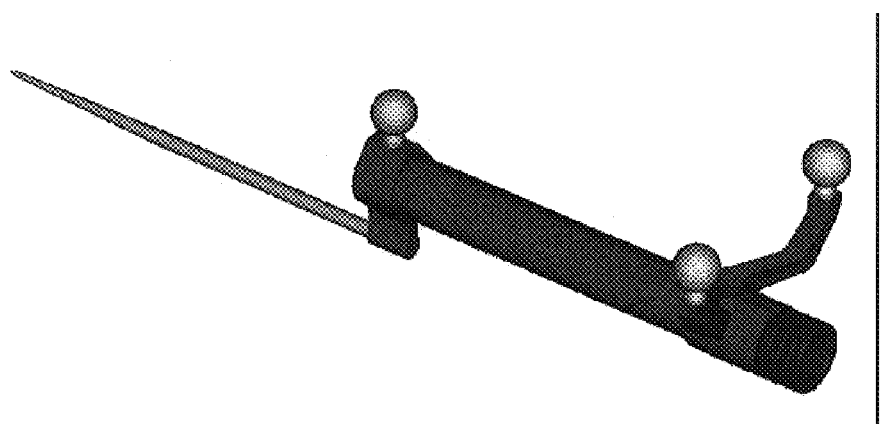
FIG. 7 depicts an alternate view of the schematic of FIG. 5.

FIGS. 3 through 6 illustrate apparatus according to an exemplary embodiment of the present invention, and FIG. 7 depicts a schematic of the exemplary apparatus of FIGS. 3-6.

Figure 3:
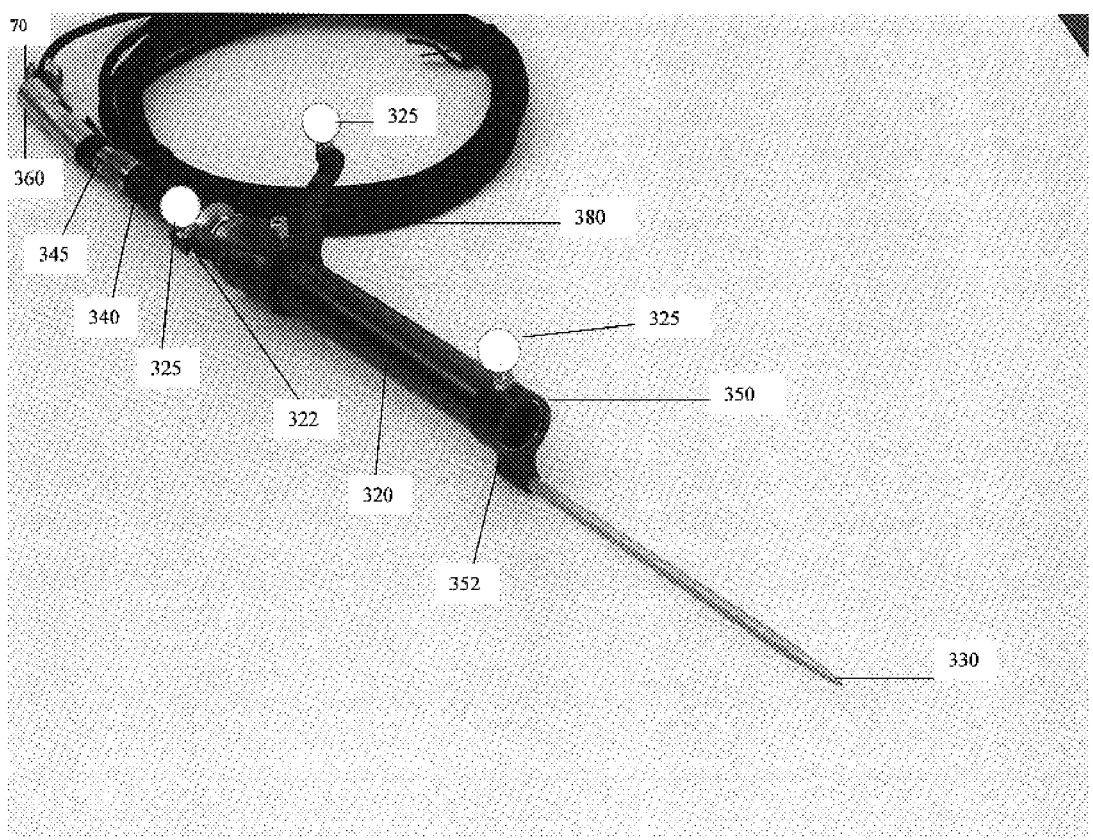
FIG. 3 depicts an example probe according to an exemplary embodiment of the present invention.

As can be seen with reference to FIG. 3, a probe according to an exemplary embodiment of the present invention has four main components, three of which are visible in FIGS. 3-6. There is a pointer tip 330, detachable from a main housing 320. The main housing 320 has three spheres 325 attached to it. There is one sphere 325 attached to the top of a front portion of housing 320 and two spheres 325 attached to a rear portion of housing 320. These spheres can be used to track the position of a probe relative to a patient's body (and any known structures of interest within it).

Within housing 320 can be inserted, for example, a camera casing (whose only visible portion in FIG. 3 is its rear end 322, but which is depicted in FIGS. 10-15 in detail). To the rear end of the camera casing a cable 340, for example, can be connected which can, for example, carry a video signal from the camera within the probe to an imaging system. In the exemplary apparatus of FIG. 3 such a camera (not seen in FIG. 3, but shown as camera 4 in FIGS. 12 and 14) can be mounted, for example, in the front of the housing 350 behind a glass lens 352. As noted, the camera can be mounted such that the tip of the detachable pointer 330 can be seen within its field of view. At the front end of cable 340, for example, can be an aperture adjustment for the camera, such as silver colored ring 345. In the depicted exemplary embodiment of FIG. 3, the terminus of cable 340, the aperture adjustment device 345 and the camera itself are collectively shorter in length than housing 320 (whose length can be, for example, a function of certain ergonomic and design factors, as described below). As a result, an extension piece 360 can be used to hold the camera assembly in place within the camera casing. At the back of extension piece 360 a locking device 370 can be utilized to hold the camera assembly in place within the camera casing in a fixed (frontward-backward) position relative to the housing 320, as described below. Additionally, the camera (within the camera casing) can be fixed at a known (rotational) orientation relative to the housing 320 by use of, for example, a bevel in the rear 322 of the camera casing, as described below, which can, for example, mate with a protrusion out the back of the housing 320, thus allowing the camera casing 322 to be locked in place relative to the probe housing 320. This can be implemented, for example, by means of an attachment device, such as, for example, screw 380 in FIG. 3.

Figure 4:
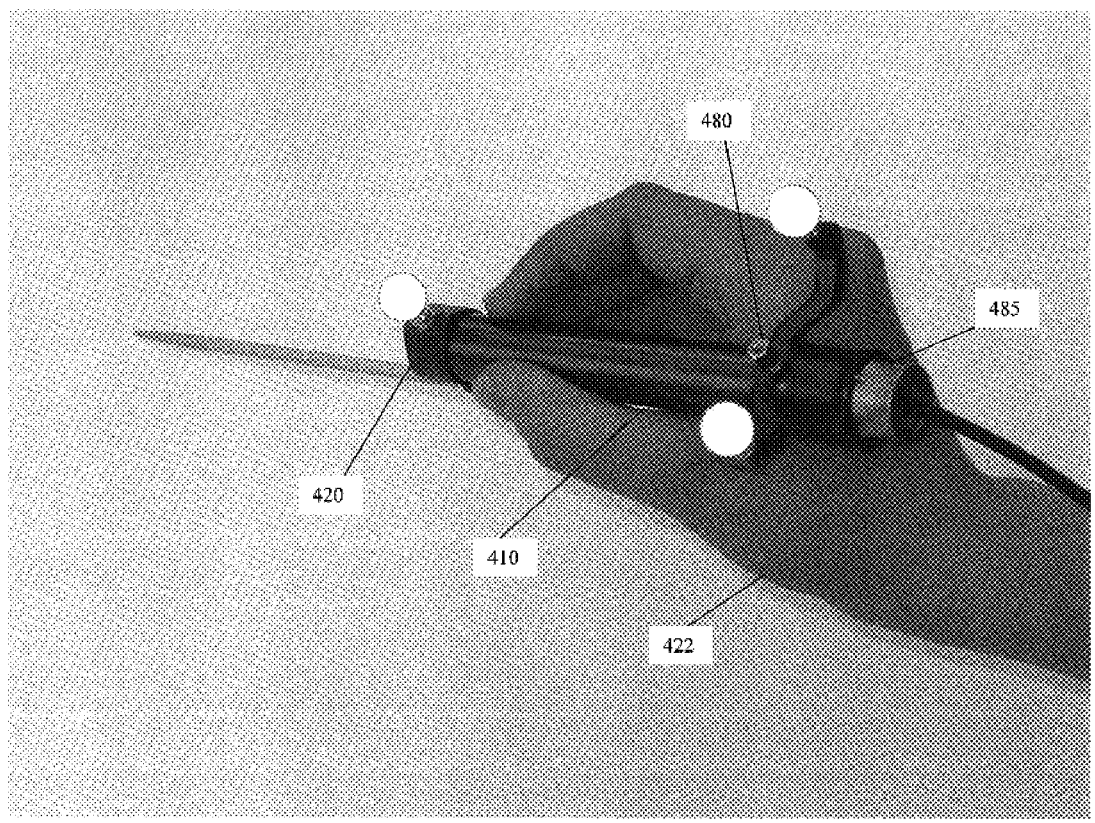
FIG. 4 depicts the example probe of FIG. 3 as held in a user's right hand.

FIGS. 4-6 depict the probe of FIG. 3 as held at various angles by a user. With reference to FIGS. 4 and 6, it can be seen how, in exemplary embodiments according to the present invention, the probe is easily held within a user's hand, in much the same way that a pen or pencil is held. With reference to FIG. 4, the rear of probe housing 410 can rest in the "valley" of a user's hand between the thumb and index finger, and such thumb and index finger can hold the front of the probe 420 as it rests on a user's middle finger. As can be seen from FIGS. 4-6, the dimensionality of the probe is such that it is an easily maneuverable hand-held device.

Also visible in the exemplary device of FIG. 4 is a protrusion 485 out from the back of probe housing 410 which can, for example, dock the camera casing 422 in a desired rotational orientation by mating with a bevel (not clearly visible in FIG. 4) in the rear of the camera casing 422, as described. Once in the desired position, the camera casing can, for example, be locked in place by tightening screw 480. The protrusion 485, tightening screw 480 and bevel will be described in greater detail with reference to FIG. 13, below.

Exemplary apparatus according to an exemplary embodiment of the present invention will next be described with reference to FIGS. 8-15. As noted above, an exemplary probe according to an embodiment of the present invention can consist of four parts: (1) a detachable pointer tip; (2) a housing (i.e., the portion of the probe where a user grasps it) which houses the camera assembly; (3) a camera which is embedded and fixed in a casing; and (4) one or more navigational markers, such as, for example, the three tracking balls 325 depicted in FIG. 3.

FIGS. 5 and 7 are graphic drawings of a probe according to an exemplary embodiment of the present invention, and FIG. 6 is the example probe of FIG. 4 seen from a different angle.

Figure 8:
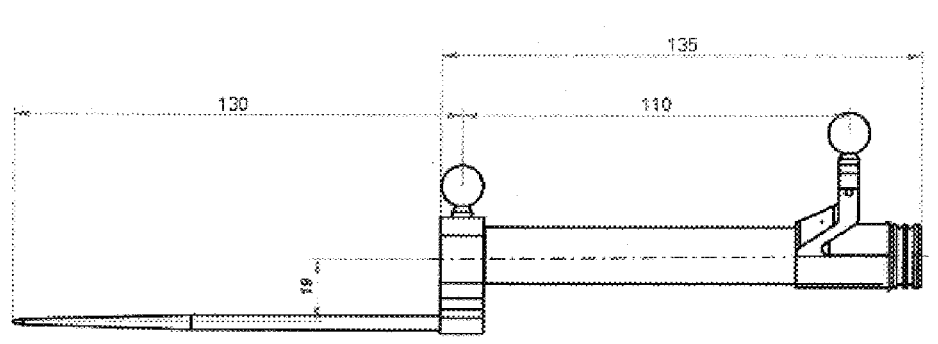
FIG. 8 depicts various exemplary dimensions of an example probe according to an exemplary embodiment of the present invention.
Figure 9:
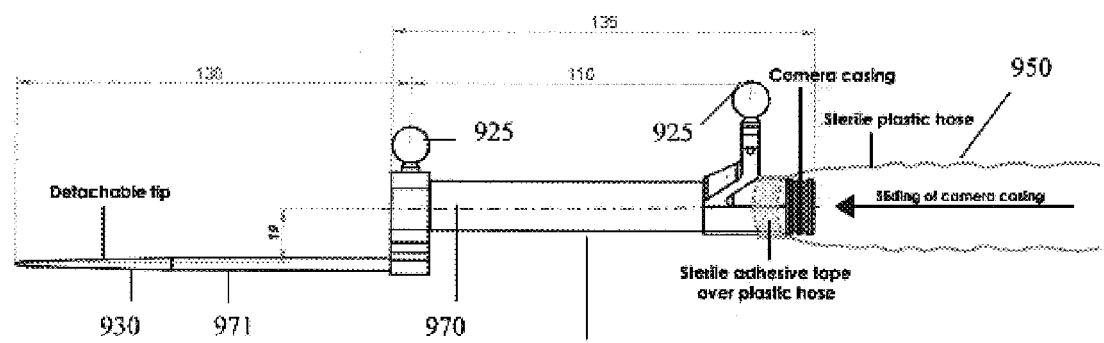
FIG. 9 depicts the exemplary probe of FIG. 8 covered for use in a sterile environment.

With reference to FIGS. 8-9, some example dimensionalities of a probe according to an exemplary embodiment of the present invention will next be discussed. Inasmuch as FIG. 9 includes the information depicted in FIG. 8, these exemplary dimensionalities will be discussed in connection with FIG. 9. FIG. 8 provides an enlarged view, with only the probe itself being depicted, for close inspection.

FIG. 9 depicts three visible components of an exemplary probe. A detachable tip 930, a housing 920 and two (out of three) trackable spheres 925. As can be seen, exemplary dimensions are shown for this probe as being 130 mm for the detachable pointer tip length, 135 mm between the rear end of the probe housing and its front, and 110 mm between the axes of the front and rear pair of trackable spheres 925 (all lengths in FIGS. 8 and 9 are in millimeters). The depicted dimensions are merely exemplary, and can be widely varied according to design as well as ergonomic considerations. The central axis 970 of the probe housing 920 is, in this exemplary embodiment, offset by 19 mm from the central axis 971 of the detachable pointer tip 930. These dimensions are interconnected as follows. The offset (in the depicted example 19 mm) between the probe housing axis and the pointer tip axis, in combination with the length of the pointer tip, determines the apparent size of, and thus how prominent within the camera's view, the pointer tip will be.

In alternative exemplary embodiments of the present invention other offsets can be used, such as, for example, offsets in the range of 15-20 mm, depending upon the length of the pointer tip and user preference. The length of the probe housing 920, determined by either the distance between the central vertical axis of the front trackable sphere 925 and the midpoint of the two vertical axes of the rear trackable spheres 925, shown in FIG. 9 as 110 mm, or by the distance from end-to-end of the probe housing 920, shown in FIG. 9 as 135 mm, can also vary according to ergonomic or design concerns.

In certain exemplary embodiments according to the present invention such probe housing length will have a lower limit as a function of the tracking device used. This is because certain tracking devices, such as, for example, the Polaris system, require a minimum lateral distance of 50 mm between a front tracking ball and a pair of rear tracking balls in order to adequately track a device, and an upper limit to that distance of approximately 300 mm, beyond which it becomes more difficult to accurately track a device. Within these limits, or other limits as may be determined by alternative tracking systems, the probe housing length dimensionality is a function of various user concerns and can be effectively any length which supports tracking.

As can be seen in the exemplary probe of FIG. 9, there is an offset in the vertical direction between the center of the front tracking ball 925 and the centers of the rear pair of tracking balls. This is also done, in exemplary embodiments of the present invention, so as to facilitate tracking. As is known in the art, for most tracking systems it is preferred to have the plane of the tracking balls perpendicular to the line of sight of the tracking system (usually, for example, a line 45° below the horizontal in the frame of reference of FIG. 9, originating from the upper left hand corner). Because a probe can often be held at an angle off of the horizontal by a surgeon, but not at a full 45° angle above the horizontal (which would make the probe exactly perpendicular to the exemplary line of sight), in exemplary embodiments of the present invention an offset between the heights of the front and rear pair of tracking balls can be used. Such an offset can, for example, orient their mutual plane to be at a positive angle up from the horizontal (positive in the sense that the probe tip held downward relative to the rear of the probe housing is defined as a positive angle of rotation) which can enhance the perpendicularity of the tracking ball plane relative to such an exemplary line of sight of a tracking system, thus enhancing the visibility of an exemplary probe to a tracking system.

In exemplary embodiments according to the present invention, probe housing 920 can be autoclaved, and a sterile hose 950 can be attached to its rear end, as depicted in FIG. 9. Because the housing and pointer tip are used in surgical fields, they are preferably of non-toxic, non mutagenic, and non corrosive materials. In an exemplary embodiment of the present invention they can be made of titanium. In the operating room, a non-sterile camera (as most exemplary cameras cannot be safely autoclaved without damaging them) can, for example, be slipped through sterile hose 950, and inserted and locked inside the probe housing 920 as shown.

Housing 920 can, for example, contain a piece of glass or similar material in the front, which prevents the camera from getting in touch with or interacting with the sterile environment. In exemplary embodiments according to the present invention, such piece of glass can, for example, be made from a high transparency material, such as, for example, quartz, and can, for example, have minimal distortion properties of the incoming light which it passes to the camera lens. The glass or similar material can, in exemplary embodiments of the present invention, fit snugly in the housing, sealing off the camera from the surgical field.

Figure 10:
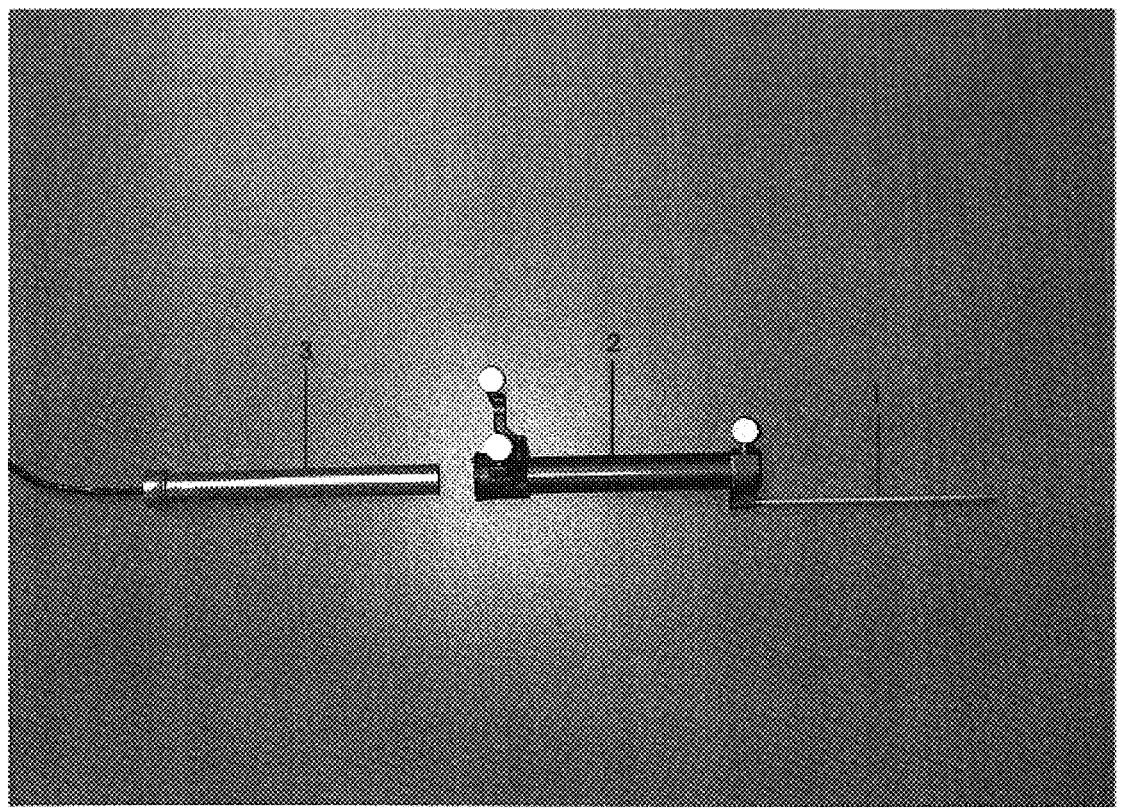
FIG. 10 is an expanded view of the exemplary probe of FIG. 3.
Figure 11:
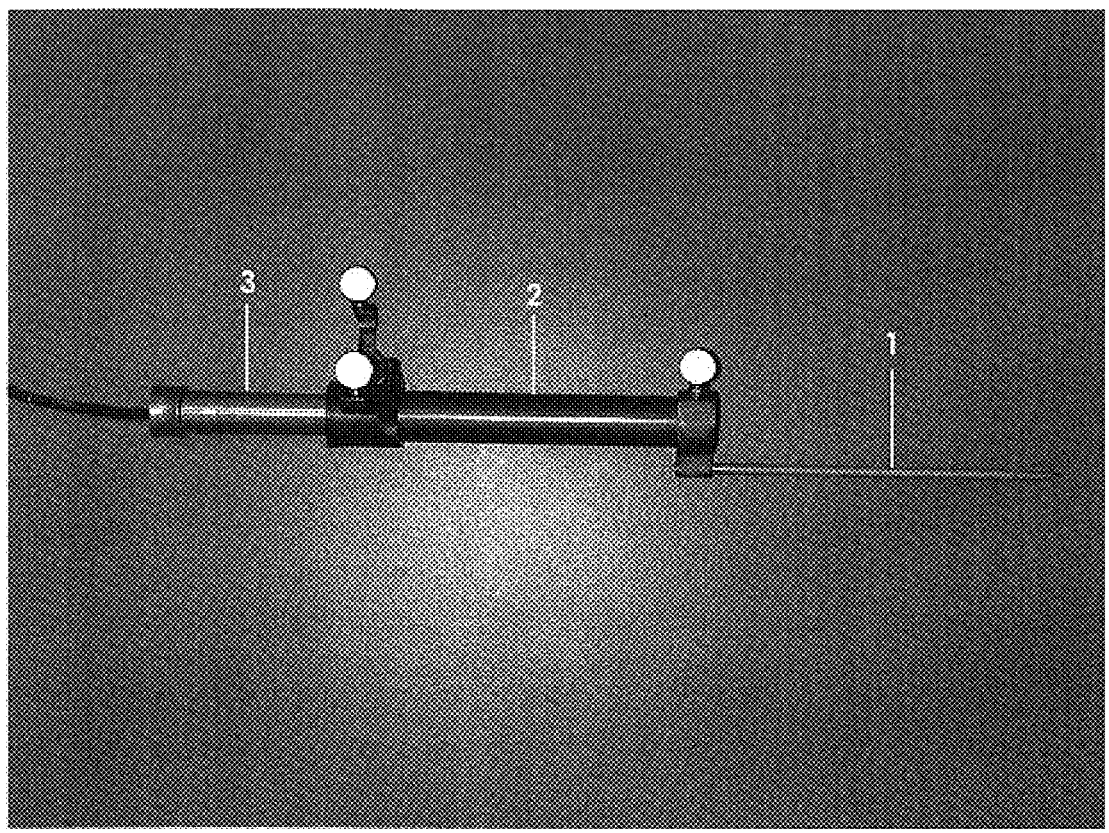
FIG. 11 is a semi-expanded view of the exemplary probe of FIG. 3.
Figure 12:
FIG. 12 depicts a front view of various parts of the exemplary probe of FIG. 3.
Figure 13:
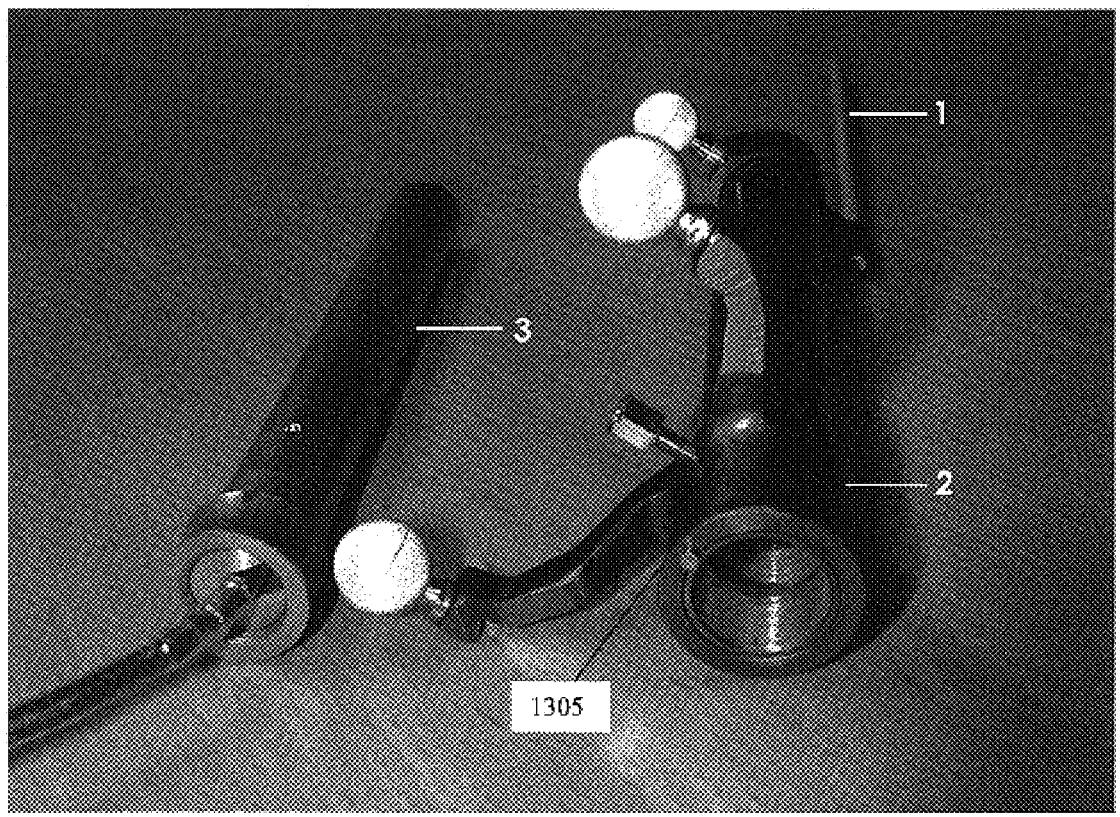
FIG. 13 depicts a rear view of various parts of the exemplary probe of FIG. 3.
Figure 14:
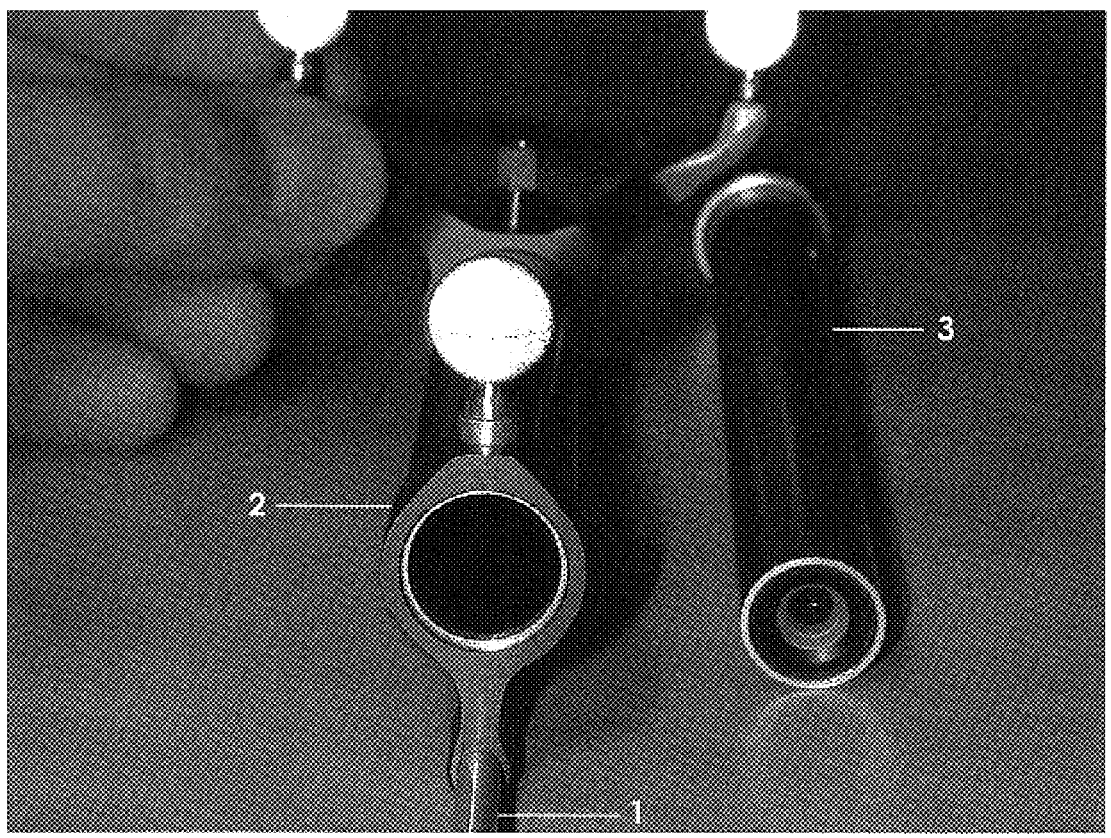
FIG. 14 is an alternate front view of the disassembled exemplary probe depicted in FIG. 12.
Figure 15:
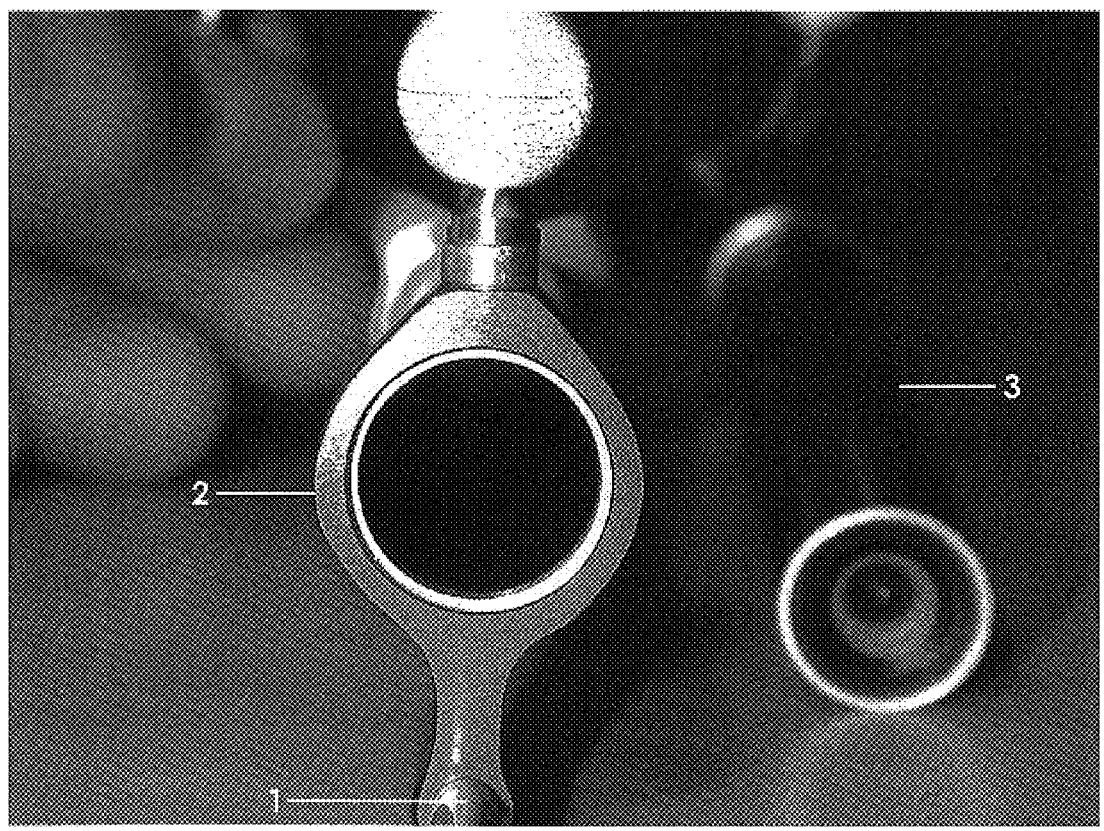
FIG. 15 is a close-up view of the disassembled exemplary probe of FIG. 14.

With reference to FIG. 10, an exemplary probe can be, for example, constructed in a way that ensures that camera 3 (in its casing) can be inserted in only one possible way into probe housing 2. A locking mechanism can be provided to lock the camera assembly 3 in a fixed position relative to housing 2. Such a locking mechanism can be best seen with reference to FIG. 13, where, for example, a small bevel 1301 can be notched in the rear of camera casing 3 such that when slid into the housing 2, such bevel fits neatly over protruding plug 1305, thus holding the camera in one rotational orientation. By screwing down screw 1310 such that camera casing 3 is secured, camera casing 3 is assured to always be in the same fixed position relative to housing 2. This insures that the camera (which is fixed relative to camera casing 3, as described above) will always be correctly calibrated, inasmuch as when camera casing 3 is locked into position, the distance from the front of the camera (which is the origin of the camera's frame of reference) to the tip of the detachable pointer and to the centroid of the navigational markers (for example, the tracking balls as described above) can be known (having been previously measured during calibration).

Besides providing real time video images of a surgical field, in exemplary embodiments according to the present invention a probe can be, for example, used as a magnification device, implementing digital zoom functionality, and as a navigation device. To implement this functionality the pointer tip can be removed, for example, to provide the camera an unobstructed view and leave additional space for hands and instruments which may be operating in front of the probe. During zooming (digital and/or optical, as may be the case in a given exemplary embodiment according to the present invention) the augmented 3D computer graphics can be, for example, adapted in size and shape according to the magnification of the camera image.

If such an exemplary camera's resolution is high enough, this set-up could, in exemplary surgical scenarios, even replace optical magnification devices such as microscopes or heads-up lenses. With such a high resolution camera and an associated digital zoom capability, the methods and apparatus of the present invention could, for example, revolutionize microsurgery, allowing magnifications in excess of those available via conventional optical systems, with, given appropriate image processing technology, less optical distortion of the incoming light.

In other exemplary embodiments according to the present invention the real time images as well as the virtual images can be stereoscopic. In such embodiments a dual camera arrangement could be, for example, implemented to achieve online stereoscopic images, which could, for example, then be viewed on a monitor with polarized, shutter or color-coded 3D glasses, or on any other 3D display using techniques as may be known in the art. These stereoscopic images can, for example, then be combined with stereoscopic virtual images formed from the pre-operative scan data, using known techniques. In such exemplary embodiments this technique can allow for a greater sense of depth, and can facilitate operating in surgical fields which can be accessed by a probe, but where no direct line of sight to the surgeon's eyes is at all available, thus requiring a surgeon to use only the display to navigate and visually interact with the patient.

Process Flow

Figure 16:
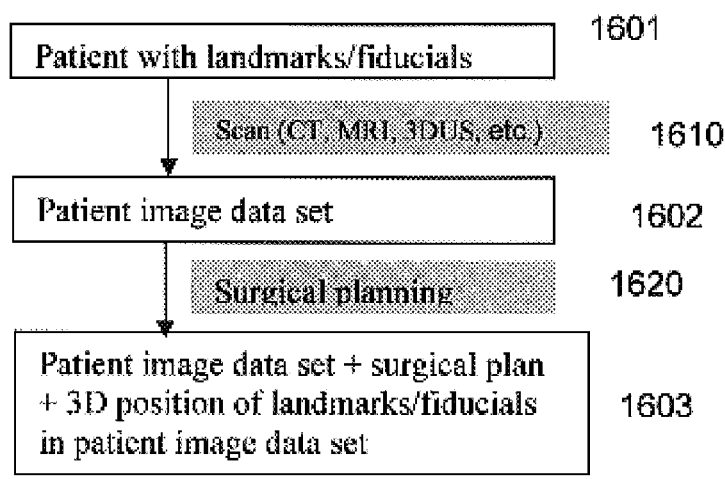
FIG. 16 is an exemplary process flow diagram for a pre-operative planning process according to an embodiment of the present invention.

Process flow according to an exemplary embodiment of the present invention will next be described. FIG. 16 depicts process flow for an exemplary pre-operative planning process for surgical navigation. At 1601, a patient can be, for example, outfitted with landmarks or fiducials, which can be, for example, objects in a variety of shapes, such as, for example, rings, squares or other shapes which are readily identifiable, and which show up on scans. Such fiducials can be made from various materials as are known in the art. At 1610, the patient undergoes scanning to create pre-operative imaging data. In the exemplary process depicted in FIG. 16, a patient is undergoing a multi-modal scan comprising computerized tomography ("CT"), magnetic resonance imaging ("MRI"), and three-dimensional ultrasound ("3DUS"). As a result of this scanning, at 1602 there exists a patient image data set which is a three dimensional data set representing the anatomical area of the patient relevant to the desired procedure. At 1620, surgical planning can be implemented as is known in the art, and the cumulative result of 1601 through 1620 is a patient image data set comprising (i) imaging data of the relevant area/anatomy as processed by a surgical plan, and (ii) the three-dimensional position of the landmarks/fiducials within the multi-modal scan space.

Figure 17:
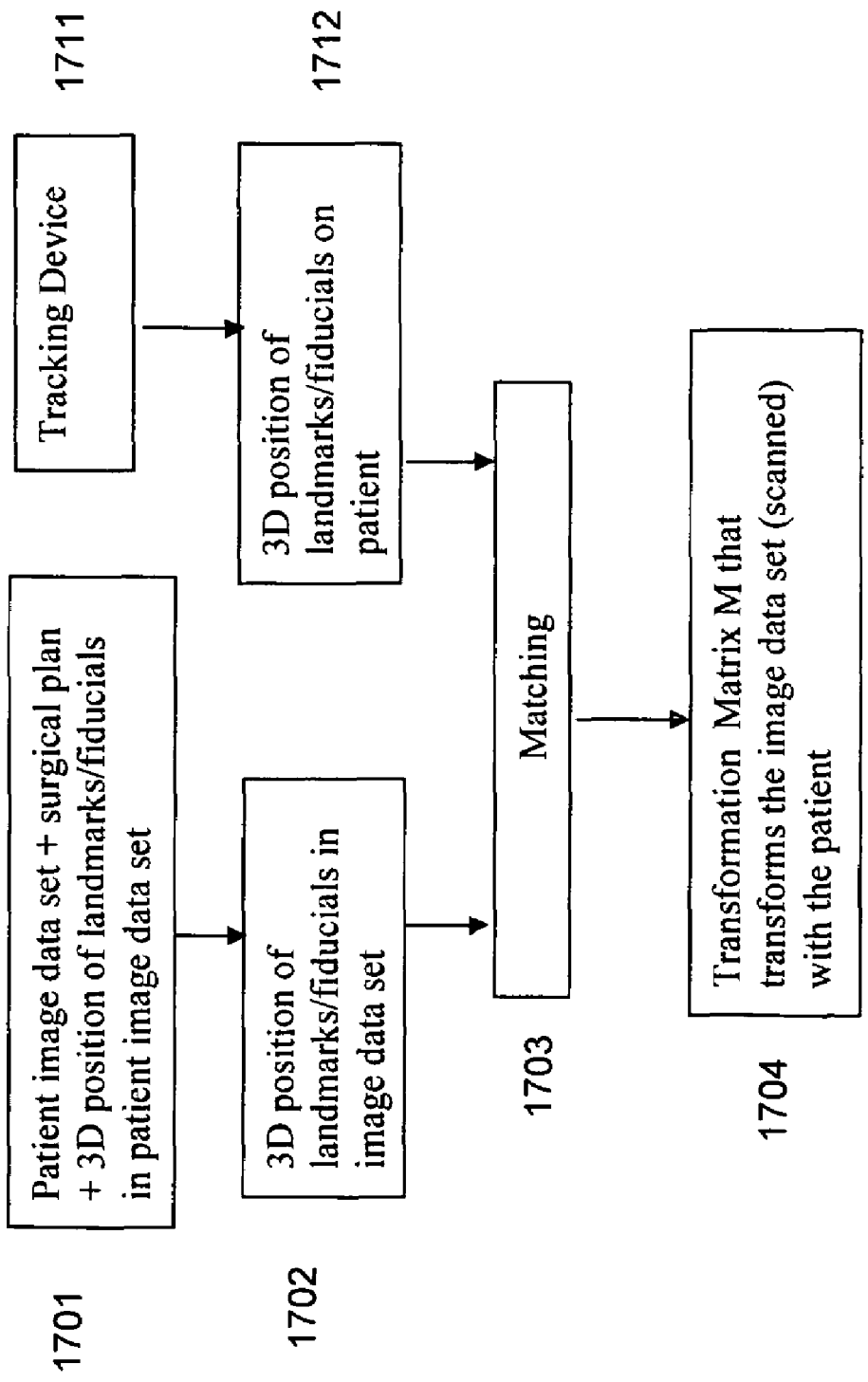
FIG. 17 is an exemplary process flow diagram for an example registration process according to an exemplary embodiment of the present invention.

Given the completion of an exemplary pre-operative planning process as depicted in FIG. 16, with respect to FIG. 17 an exemplary registration process will next be described. A registration process seeks to align or co-register a patient image data set, such as for example, that from 1603 of FIG. 16 with the physical patient in a video camera's 3D space such that the patient image data set can be superimposed over real time video from the video camera with minimal error. Such real time video can be used, for example, in conjunction with pre-operative imaging data, for navigation during surgery. For obvious reasons, such an augmentation of real time video with pre-operative 3D imaging data for surgical navigation only works if the super-position is accurate. In other words, if the 3D space of the pre-operative imaging data can be co-registered with the 3D space in which the patient and the video camera are oriented during surgery with minimal error, a useful result can be generated. Therefore, with reference to FIG. 17, 1701 and 1702 (appearing on the upper left hand side of the process flow diagram) represent the processing of pre-operative imaging data, and 1711 and 1712 (appearing on the upper right hand side of the diagram) represent the processing of real-time, or actual, physical data. These two parallel data streams can then be matched, for example, at 1703.

Beginning with 1701, a patient image data set, e.g. from 1603 of FIG. 16, can be loaded. At 1702 three-dimensional positions of the landmarks/fiducials from the patient image data set can be extracted. At 1711, a tracking device, such as, for example, NDI's Polaris™ can be engaged, and at 1712 actual 3D positions of the landmarks/fiducials on the physical patient can be determined within the reference frame of the tracking device. The 3D position of landmarks/fiducials from 1712 and 1702 can be correlated in 1703 such that at 1704 a Transformation Matrix M can be created that can, for example, operate upon the pre-operative patient image data set to effect a co-ordinate transformation to co-register objects in the frame of reference of the tracking device, which will be the same frame of reference as that of the camera, with objects in the frame of reference of the scan data.

Figure 18:
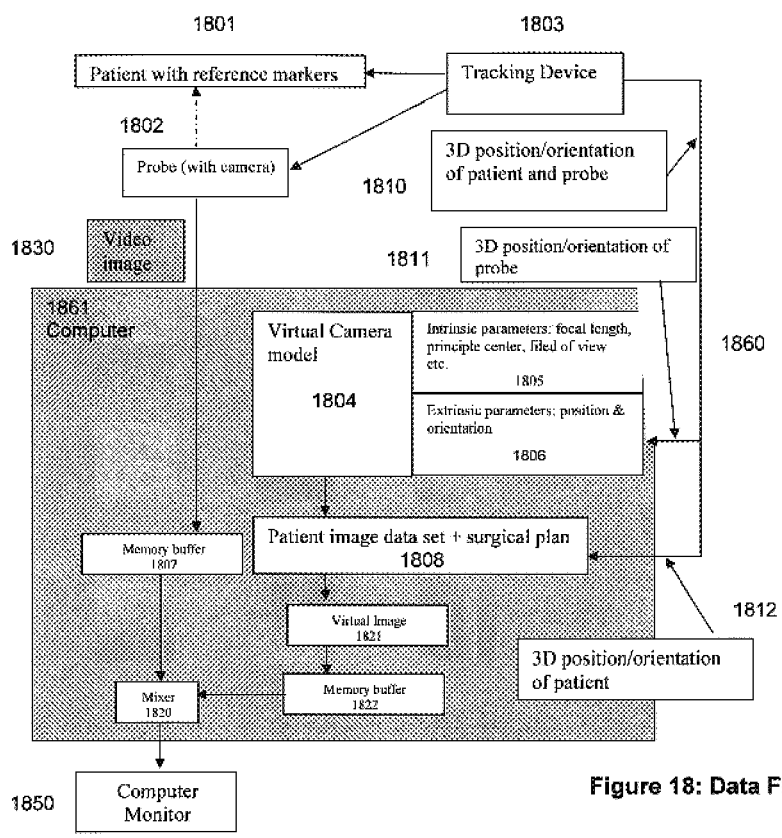
FIG. 18 is an exemplary process flow diagram for intra-operative navigation according to an exemplary embodiment of the present invention.

During surgery, process flow can be, for example, as shown in FIG. 18. The camera within the probe 1802 sends real time video of the patient 1801 to a computer 1861, where it can be stored, for example, in memory buffer 1807. The probe's 3D position and orientation can be detected by a tracking device 1803 by, for example, tracking markers on probe 1802. A virtual camera 1804-1806 can be generated, for example, by computer 1861 pursuant to a system program. Its intrinsic parameters 1805 can be identical to those of the real camera in probe 1802. Such parameters can be, for example, determined through a precise calibration process beforehand, using means known in the art. Its extrinsic parameters (position and orientation) 1806 can be updated via the tracking device 1803, which can, for example, provide the 3D position/orientation of probe 1811 and the 3D position/orientation of patient 1812 (also shown as combined data 1810 which is output from the tracking device 1803, which is then split into probe data 1811 and patient data 1812).

A patient's image data set 1808, including the surgical plan as described above, can be, for example, loaded from a surgical planner, such as, for example, Volume Interactions' VixDexter™ or RadioDexter™ (not shown), and registered to the patient using, for example, a transformation matrix which can be output via a registration process as described in connection with FIG. 17. Such a registration can be, for example, transformed to a reference marker system rigidly linked to patient 1801 so that registration can be maintained during surgery by tracking reference system 1801 via tracking device 1803. A virtual camera 1804 can, for example, generate a virtual image 1821 of a patient image data set and surgical plan 1808 according to updated tracking data from both probe 1802 and patient 1801 as indicated by elements 1811 and 1812, respectively. Virtual image 1821 can be sent to a memory buffer 1822, and then mixed by the mixer 1820 with a video image stored in memory buffer 1820 and output to monitor 1850 for display. Transparency, color, size and other properties of the virtual and real images can be controlled, for example, by adjusting various parameters used in the program.

Display Functionalities

Figure 19:
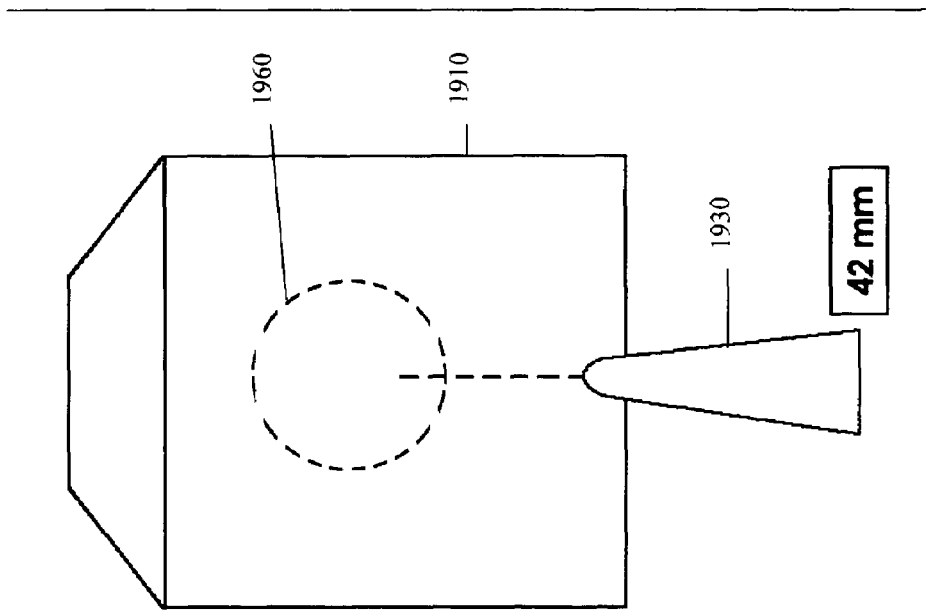
FIG. 19 is a schematic drawing of a dynamic display of a computer generated object's distance from a probe tip according to an exemplary embodiment of the present invention.

FIGS. 19-24 depict screen shots of exemplary displays according to exemplary embodiments of the present invention. With reference to FIG. 19, the presentation of a dynamic distance to a virtual object is depicted. FIG. 19 depicts a view from the camera according to an exemplary embodiment of the present invention. Within that view, detachable pointer tip 1930 is visible, as well as virtual object 1960. However, the virtual object, sphere 1960, is not visible from the location within the surgical field that the camera occupies. All that can be seen, for example, is rectangular object 1910. However, from preoperative scan data, it is known that spherical object 1960, for example, lies within visible rectangular object 1910. The functionality of the present invention allows a user, given a certain location of the camera and detachable pointer tip 1930, to see a continual readout of the distance between the detachable pointer tip 1930 and an invisible, but known to be present, virtual object 1960, such as, for example, sphere 1960 in FIG. 19.

In this sense, in exemplary embodiments of the present invention a user can see beyond the field of view of the probe's camera through opaque surfaces within the surgical view to objects which are known to be present from scan data, and which can be thus displayed as virtual objects within a displayed scene. (This functionality is somewhat analogous to "X-Ray Vision," and for this reason the exemplary embodiment described below is marketed as the "DEX-Ray™" system. For illustrative purposes, this functionality can be depicted with a model of a human skull, and a variety of three-dimensional geometric objects inserted in the skull cavity, as shown, for example, in FIGS. 20-24.

Figure 20:
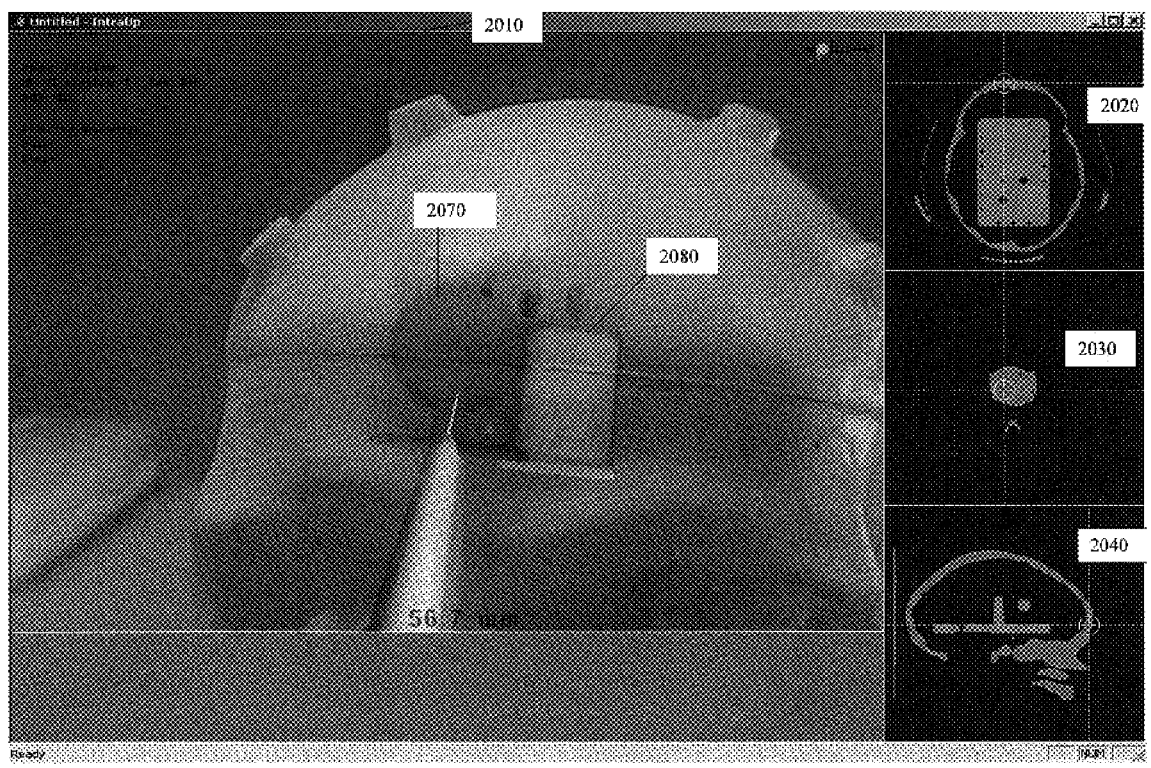
FIG. 20 depicts an exemplary screen shot according to an exemplary embodiment of the present invention illustrating, inter alia, the function depicted in FIG. 19.

With reference to FIG. 20, an exemplary screen shot of an example display according to an exemplary embodiment of the present invention is shown. There is a main screen 2010 which depicts the combined real-time images acquired by the camera within the surgical field with virtual object images generated from pre-operative scan data. Additionally, two-dimensional images generated from such scan data are also shown in three smaller screens at the right of the display. These comprise an axial plane 2020, a coronal plane 2030, and a sagittal plane 2040. As can be seen within each of the axial 2020, coronal 2030 and sagittal 2040 planes respectively, there appears a cross-hairs within a circle icon (here shown in white) which indicates the real-time position of a probe tip relative to the images then shown in each of the 2D images.

Thus, with reference to FIG. 20, and assuming for illustrative purposes a co-ordinate system where the x axis is a horizontal line across the image display, the y axis is perpendicular to it extending into the depth of the image, and a z axis is a vertical line perpendicular to each of the other axes, axial plane 2020 depicts an xy plane which contains a horizontal slice of the skull and its contents at the fixed z value then occupied by the tip of the probe. It is noted that axial plane 2020 depicts the view from above the skull. Thus, within such axial plane there is seen a rectangular object which shall be more fully described below. Similarly, coronal plane 2030 depicts an xz plane containing a vertical slice of the skull parallel to the surface of the display at the y value occupied by the tip of the probe (the term "tip of the probe" or "probe tip" within this discussion is understood to refer to the tip of the pointer, and the term "pointer tip" or the like will be used interchangably with such terms). Finally, display 2040 depicts the saggital, or yz plane, which is a vertical slice of the skull perpendicular to the plane of the image (i.e., a plane tangential to the forehead of the skull) at the x coordinate occupied by the probe tip.

Noteworthy with respect to FIG. 20 is the distance 2015 (56.7 mm) between the pointer tip and the sphere (which is, in the context of a closed skull, known only from the preoperative data) which is displayed as a virtual object within main display 2010. This distance is along a virtual ray extending in the direction of the pointer tip to the surface of the virtual object. Moreover, for ease of discernment a user can, for example, choose the colors by which virtual objects are depicted in the combined image, so as to better distinguish them one from the next. This feature is illustrated in FIG. 20 by the depiction of virtual sphere object 2070 in red and virtual cylinder object 2080 in green. As noted, in this exemplary screen shot the main display presents at the bottom of the real-time image the distance between the tip of the pointer and the virtual sphere object 2070 as 56.7 mm.

Figure 21:
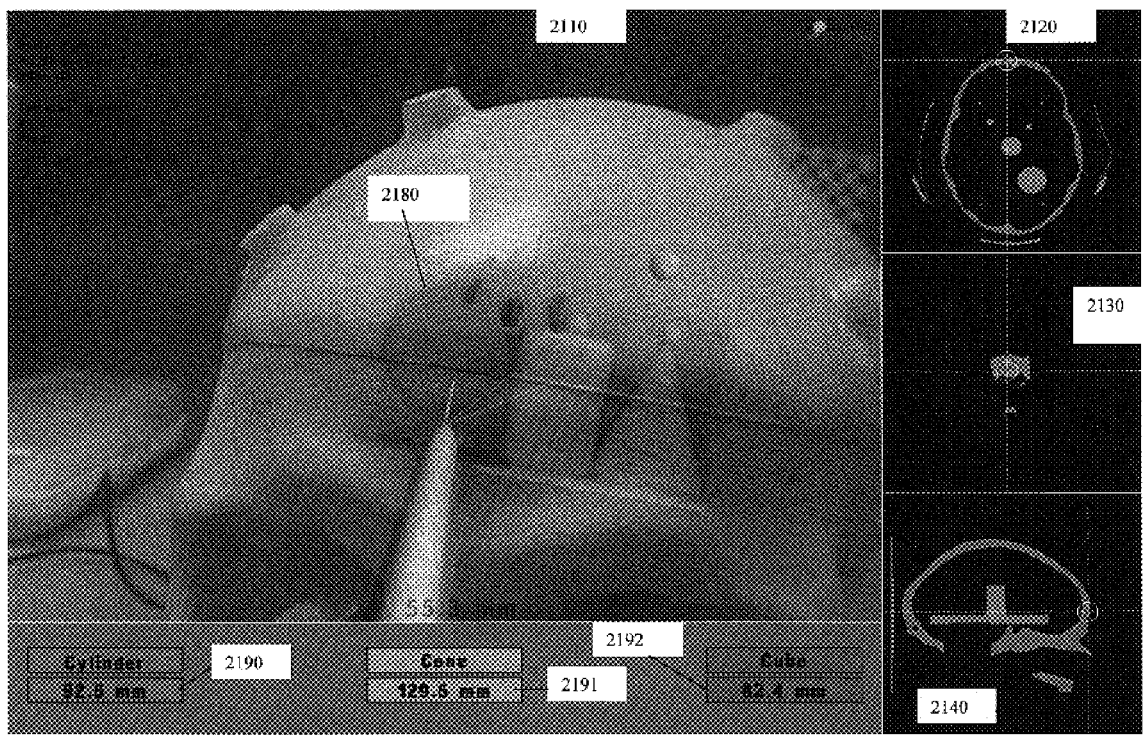
FIG. 21 depicts an exemplary screen shot according to an exemplary embodiment of the present invention illustrating the functionality depicted in FIG. 19 as well as the dynamic distance to various pre-selected 3D marker points.

A similar display is shown in FIG. 21 with a few notable differences. Underneath the real-time image in the main display window 2110, there are three color coded displays, each showing a name of a virtual object and a distance from the probe tip to a user designated landmark point on or near that virtual object. Such points can be set anywhere in the 3D data set, i.e., on or off the virtual object. To track the running distance to an object, a landmark point can be set, for example, at the tip or at the center of the uppermost plane of the object, as shown in FIG. 21. These landmark points are the three spherical objects connected to the probe tip via rays, where two of the three spheres appear at the tops of the cylinder and the cone, respectively. The third sphere appears hovering to the upper right of the cone, and in actuality is set at the top of a cube object, which has been set too transparent to see clearly. The cube object is visible in FIGS. 22 (real image as skull top has been removed) and 23 (virtual image of cube, transparency set to be more visible).

More particularly, beginning on the bottom left under the main display window 2110 there are a pair of red colored rectangular windows 2190. These are the landmark name and landmark distance readout bars, respectively. The upper rectangular window displays the name of the designated landmark, in this example a (point on a) cylinder, and the distance from it to the pointer tip, here 92.5 mm. This is the virtual cylinder seen to the right of the probe, in the center of main window 2110. A similar rectangular window pair 2191 in the bottom center designates an exemplary point on a cone (seen to the right of the cylinder) whose distance is 129.5 mm, and finally, on the bottom right of the main display, there is a designated point on a cube object whose distance is 82.4 mm from the tip of the probe. It is noted that none of the designated landmarks are on the virtual sphere displayed as virtual object 2180 within main display 2110. The distance 2115 along the direction of the pointer tip to that virtual sphere is 55.8 mm. In exemplary embodiments according to the present invention, the distance to the closest virtual object in the data set is always displayed at the bottom of the main display window, and the distances to any landmark points in the rectangular landmark name and landmark distance readout bars under the main display window.

Thus, FIG. 21 illustrates an example of the functionality according to an exemplary embodiment of the present invention whereby a user may designate one or more objects known to exist from the preoperative scan data to be displayed, and one or more landmarks to be set with the running distance between the pointer tip and such landmarks to be displayed at all times. Therefore, the numbers in the bottom rectangular window of each of 2190 through 2192, which are distances between the probe tip and the three designated landmarks will change as a user moves the probe. In the exemplary display of FIG. 21, as noted, the cube object has been turned off, or made transparent, and is thus not displayed, however the landmark point set at its tip is still tracked and the distance of that point from the probe tip is thus displayed. As noted, the reason why the distance to the virtual red sphere is depicted in the main display is that it is the object with the closest distance to the pointer tip along the virtual ray extending from the pointer tip along the direction of the pointer tip's axis. This illustrates an exemplary functionality according to an exemplary embodiment of the present invention, whereby the distance along such virtual ray to the point where such ray intersects the nearest virtual object is always displayed in the main display.

In FIG. 21 the three auxiliary planes showing sections of preoperative scan data, being the axial 2120, the coronal 2130, and the sagittal 2140, are also displayed, as described above with reference to FIG. 20.

Figure 22:
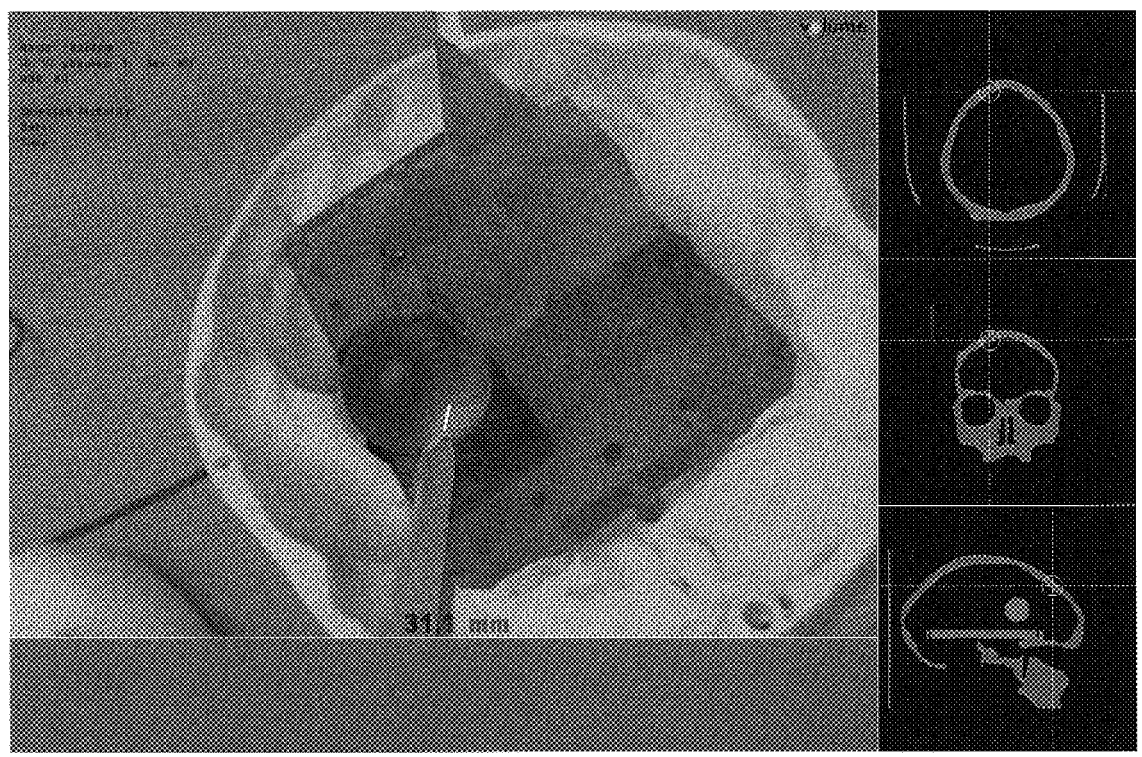
FIG. 22 depicts an alternate view of the exemplary scene depicted in FIGS. 20 and 21 with the upper portion of the model's skull removed so as to reveal the example objects located inside.
Figure 23:
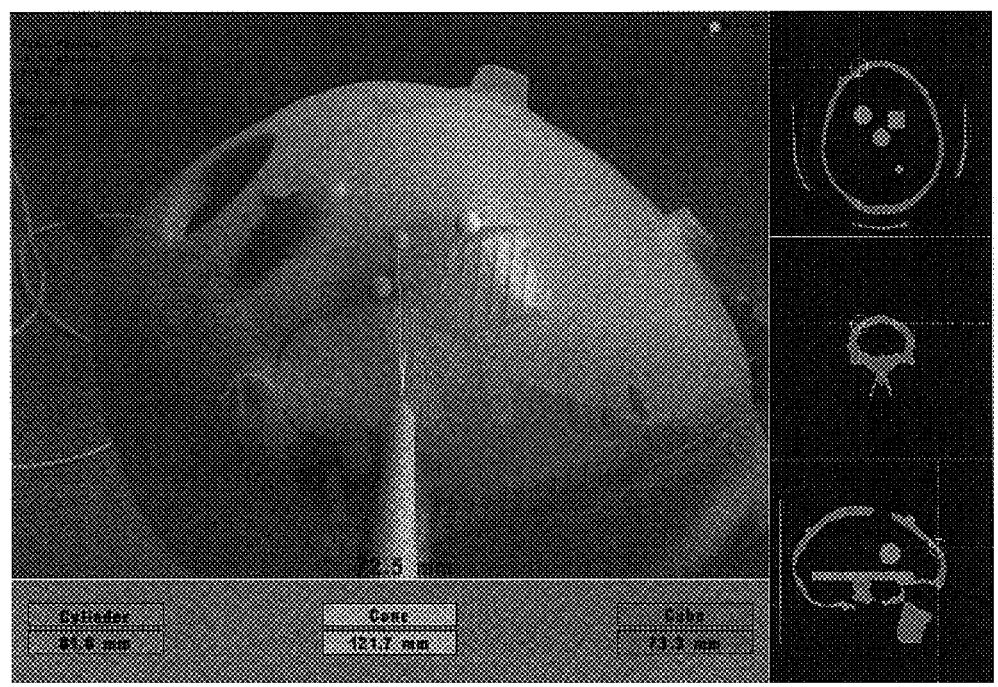
FIG. 23 depicts an alternate view of the exemplary scene depicted in FIG. 21.
Figure 24:
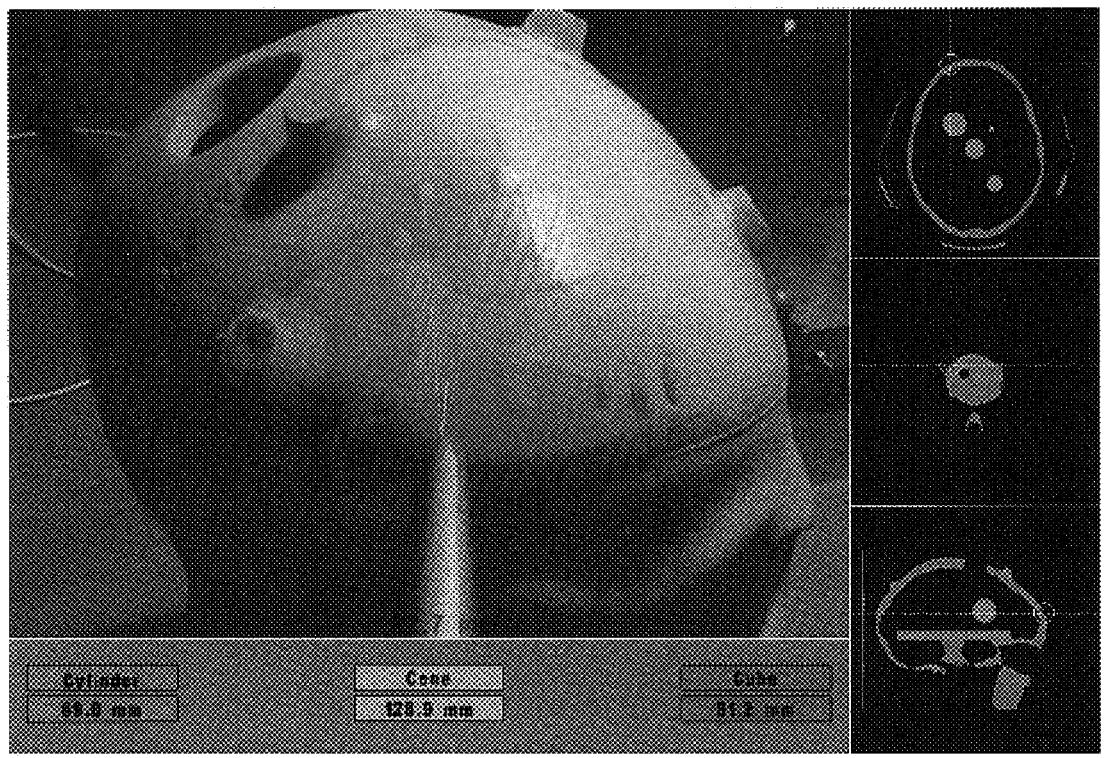
FIG. 24 depicts an alternate view of the exemplary scene depicted in FIG. 23.

With reference to FIGS. 22-24, a number of additional functionalities according to exemplary embodiments of the present invention are indicated. It is noted that in the exemplary embodiment of the present invention of FIG. 22 the axial plane depicts a view from below. FIGS. 22-24 depict an alternative illustration of a model skull with various interior objects located within it.

In FIG. 22, because the model has had the top of its skull removed, all of the interior objects within the skull are not virtual but rather seen as part of the real-time images coming from the camera. Thus, their natural color (grayish) is seen. Additionally, the red sphere has been "turned on" as a virtual object, and is thus seen in red as a virtual object while the three other objects, the cylinder, square, and cone, are only seen via the video image. Portions of the actual video image of the red sphere are also visible because of a registration error between the virtual object and the actual object in this exemplary image. If the registration in this example had been perfect the red virtual sphere would completely occlude the actual real time video image of the sphere, unless the virtual sphere had been set to display, for example, in a semi-transparent mode, in which case the underlying actual video image would have been visible through a semi-transparent red virtual sphere). All objects are sitting on a plate 2250 inserted in the interior of the model skull.

With reference to FIGS. 23-24, the top of the model skull has been returned and therefore the four objects sitting on top of the plate are once again virtual objects, as they cannot be seen by the camera within the probe. With reference to FIG. 23, the closest object along the virtual ray extending from the pointer tip is no longer the sphere but the cylinder. That distance is displayed as 72.5 mm in the bottom of the main display, whereas since the cylinder is also one of the three designated objects whose landmark points are continually tracked by the imaging system, there is also displayed, in one of the rectangular windows below the main screen, the distance to the landmark point at the top of the cylinder, which is 81.8 mm from the probe tip. The distances to the landmark points set at the tops of the cone and cube, respectively, are also displayed as described above. This is distinctively different in this exemplary embodiment of the present invention from the distance along the virtual ray to the closest available object, in this case the cylinder, whose distance is not measured with reference to a fixed landmark point, but at the closest point on an object along the virtual ray's direction to the probe tip.

Finally, with respect to FIG. 24, a similar state of affairs as in FIG. 23 is depicted. In this figure the position of the probe tip has been lowered, so that the distances to all of the designated landmarks are slightly larger. (It is noted that the amount by which the probe has been lowered can be seen with reference to the saggital display in each of FIGS. 23 and 24). Once again, with respect to FIG. 24, the closest object to the virtual ray is the cylinder, and the distance from the probe tip to the cylinder along that direction is shown to be 82.7 mm. The three designated objects of cylinder, cone, and cube, respectively, and distances to the landmark points set respectively thereon are also depicted in the lower portion of the main display.

Exemplary Embodiment—Volume Interactions' DEX-Ray™ Environment

The present invention can be, for example, implemented in an exemplary system and environment such as is depicted in FIGS. 25-31. The depicted exemplary system and environment is a version of the DEX-Ray™ surgical navigation system provided by Volume Interactions Pte Ltd, of Singapore, based on an exemplary embodiment of the present invention. The depicted exemplary environment can be, for example, bundled or integrated with a three-dimensional data set visualization system such as VizDexter™ or RadioDexter™, thus providing a complete surgical planning and navigation system and tool, or can be provided alone, for contexts where the user already has a three dimensional data set visualization system, such as, for example, the Dextroscope™ running the RadioDexter™ software. In the following description example operations in the DEX-Ray system, an exemplary embodiment of the present invention, will be described.

DEX-Ray is a surgery navigation system "surgery navigation system" that enables surgeons to visualize internal structures through an automated overlay of 3D reconstructions of internal anatomy and a live video view of a patient in the operating theatre. The system can be implemented using the following exemplary hardware: a computer with standard interface of keyboard and mouse, a tracking system, such as, for example, NDI's Polaris™, a monitor on which the system images are displayed, a probe with mini-camera fitted inside, and reference markers affixed to the probe and the patient.

Before DEX-Ray can be used for surgery navigation, a patient's virtual data needs to be prepared. Such preparation can be done, for example, with VizDexter™, RadioDexter™, or any other 3D interactive visualization system, and can include, for example, segmentation of anatomical objects of interest, placement of virtual fiducials, and storing of surgical planning data, such as pathways, landmarks, and annotations.

After the patient's virtual data has been loaded into DEX-Ray, fiducial-based registration can be carried out in order to correlate the prepared virtual data to the real patient in the operating theater. Once registration is completed, a DEX-Ray Navigation Page is presented to the user. By interacting with this page a user can either navigate in the combined video-AR world of the patient (as is illustrated in FIGS. 20-24 above) or can interact with the DEX-Ray system to set and/or modify display and other control settings.

FIG. 25 depicts an exemplary Data Loading Page. This interface can be used, for example, to load virtual patient data into the DEX-RAY™ system.

In the depicted example, the directory (i.e., "D:\Demo\Cases") where all of the virtual data is stored is shown in the field "location." In the depicted example page, all of the data files under the directory shown in the location field are listed in the case list box below it. Each data set corresponds to a given case. Each data file is indicated with a .dex extension as well as with a unique icon preceding the file name. When a file name is clicked, it is highlighted to indicate that a user is browsing the file. In the depicted exemplary embodiment, when a file name is double-clicked, all of the objects in the case are listed in the Case Viewer (i.e., right side of the depicted page), and the patient's information (e.g., Name, Sex, D.O.B) are displayed in the Patient Details boxes (below the case list box) respectively, for verification. A user can sort the data files by, for example, clicking the header "Name" or "Date" on the top of the case list box.

Once a case has been selected, all of its objects are listed in the Case Viewer box (right side of FIG. 25). In the depicted example, objects are classified into five categories as defined in the RadioDexter™ system. These are, for example, volume objects, annotation objects, measurement objects, mesh objects and alignment objects. In other exemplary embodiments any convenient object categorization can be used.

When a case has been fully loaded, a user can, for example, click on the "Next" button at the bottom right of the Data Loading Page to bring up the Registration Page. If a user tries to advance to the Registration Page without loading a case, an error message box can pop up as a warning, and advise the user to enter a case.

In summary, in exemplary operations using the Data Loading Page, a user can, for example, (i) double click a case in a case list box, (ii) verify patient information in edit boxes, (iii) load/unload or show/hide objects in a case viewer box, and (iv) click a next button to move to the Registration Page.

FIGS. 26 and 27 depict an exemplary Registration Page before and after registration, respectively. This page is used to register virtual data (i.e., data generated from pre-operative scans) to the physical (i.e., real) patient in the operating theatre. The virtual data, as prepared with a three dimensional interactive display system, such as, for example, RadioDexter™, has its own position and orientation as defined in the virtual world. Although the virtual data are reconstructed from the actual patient's scan data, their respective positions and orientations are different from those of the patient now lying in the operating theatre, whose actual position and orientation are defined in the coordinate system of the tracking system. In order to match the virtual data from the preoperative scans with the real patient so that correct overlay is possible, the former has to be co-registered with the latter.

The exemplary Registration Page depicted in FIGS. 25 and 26 is divided into four parts. The two upper parts—overlay view (left side) and tracking volume view (right side), are used for viewing and verification. The two lower parts—fiducial buttons and registration buttons (left side) and message field and next button (right side), are used for interactions between the user and DEX-Ray™ system. These views and their functions will next be described.

The overlay view (upper left quadrant) can be used, for example, to verify whether the virtual data and the live video match by viewing the overlay of these two image sources once registration has been completed. Before registration is carried out, the object associated with the alignment object is displayed in this view (here a skull) with its original position and orientation as defined in a three-dimensional data display system such as, for example, RadioDexter™. An alignment object is a series of points marked with labels as shown in the overlay view of FIG. 26. Once registration has occurred, the viewpoint will be shifted to that of the mini-camera, as seen in the overlay view of FIG. 27.

In the overlay view of FIG. 27 the fiducials chosen by the user during the registration process can be displayed on the video image of the object (i.e., the skull) while the original virtual alignment object is hidden. The fiducial with the largest registration error (here fiducial number 2) can be marked, for example, with a pair of big yellow arrows for easier identification as shown in the overlay view FIG. 27.

The tracking volume view (upper right quadrant) can be used, for example, to make sure that all of the items tracked by the tracking system are located within its optimal tracking volume. Since a 3D volume in space is displayed with 2D drawings on the screen, two views, a top view (upper box) and a front view (lower box), are employed for display. The top view depicts the viewpoint of a user looking at the tracking volume from above the tracking system while standing in front of the tracking device. The front view is the view of the user when looking at the tracking volume while standing in front of the tracking system. In each view the tracking system itself is depicted as a long rectangle. In the depicted example the shape of the tracking volume is a semi-sphere with radius of 0.5 m plus a cylinder with radius of 0.5 m and height of 0.5 m (top view shows its cross section as cut by a horizontal plane, and the front view its cross section as cut by a vertical plane). In the top view the labels around the tracking volume appearing clockwise as B, R, F and L stand for back, right, front, and left, respectively. Similarly, in the front view, the rectangle in the middle stands for the tracking system and the circle indicates a vertical cross section of the tracking volume, where the labels T, R, B, and L mean top, right, bottom and left, respectively. Each tracked item is indicated by an icon, here, for example, a small cross within a small circle. With reference to FIG. 26, one icon indicates the position of the reference markers, while the other shows the position of the probe tip. During registration, each fiducial chosen by a user can be, for example, indicated with a small cross in pink (or other noticeable color) in the depicted tracking volume for better recognition, as shown in the top and front views of FIG. 27 (color not shown).

Once registration has been completed, the registration error of each fiducial is displayed on its button, as shown in FIG. 27. Registration error, in this case, is defined as the difference between the virtual fiducial and the real fiducial chosen by the user. The error, here shown in red (i.e., in the original color drawing; difficult to see in greyscale), indicates that the associated fiducial has the largest registration error (in FIG. 27 it is fiducial number two).

On the right hand side of the fiducial buttons are three buttons related to registration: "pick fiducials," "register now," and "reset registration." When a user locates the cursor on the top of any one of these buttons, an instruction message will pop up, as shown, for example, in the bottom right corner of FIG. 26 for a cursor over the "pick fiducials" button.

A user can click the "pick fiducials'" button each time he confirms that he has located the probe tip on a real fiducial on the patient. The "register now" button can be used for unequal points matching. Unequal points matching occurs when the real fiducials picked by the user are fewer than the virtual fiducials in the virtual data. This feature is convenient when couples of the real fiducials are missing, when some of them shift substantially, or when a user feels comfortable with fewer fiducials.

The user can click the "reset registration" button to redo the registration when picking fiducials or after registration if he is not satisfied with the registration results (i.e., he feels the error is too large and thus the overlay will be off).

When registration is finished, a user can click the "next" button at the bottom of the Registration Page to open the Vector Recording Page, shown in FIGS. 29-30. If a user attempts to enter this next page without having accomplished registration, an error message box can display to so advise the user.

FIG. 28 is an exemplary process flow chart illustrating the registration process. Beginning at 2801 a user points the probe tip to a fiducial attached to the patient. At 2802 the user then clicks the PICK FIDUCIALS button, as shown at the top of the three buttons at the lower left quadrant of FIGS. 26-27. Then, if at 2804 all fiducials have been chosen, flow moves to 2809, where the user reviews the registration error. If satisfactory, flow moves to 2810 and the registration page is exited. If at 2809 registration error is not acceptable, process flow moves to 2808 and it is determined if the error associated with only one or with more than one fiducial is unsatisfactory. If only one, at 2807 that fiducial is reregistered and the loop beginning at 2802 is re-entered. If the registration error of more than one fiducials are unsatisfactory, then, at 2805, registration is reset, and more than one fiducials are rechosen.

If at 2804 all fiducials have not been chosen, then flow moves to 2803 to determine if less than the number of virtual fiducials can be used, i.e. if unequal points matching is desired. If yes, flow moves to 2806 where the REGISTER NOW button is clicked, and flow then proceeds through 2809 to the end of registration. It is noted that the number of fiducials in any case must generally be no less than six for acceptable accuracy, but this may vary with more sophisticated registration techniques. At 2803 if unequal points matching is not desired, flow moves to 2802 and more fiducials are chosen so that the number of virtual and actual fiducials are equal. Once this is accomplished, process flow returns to 2804 and on to 2809 where the user once again evaluates the registration error, as described above, either returning to 2808 or exiting via the "Next" button at 2810 to the Vector Recording Page.

FIGS. 29 and 30 depict an exemplary Vector Recording Page. This interface can be used, for example, to record a relatively vertical vector that can be used to control cursor movement in the Navigation Page (FIG. 31), as described below. Since cursor movement in the Navigation Page can be, for example, controlled by the probe as though the probe moved in a virtual plane, it is necessary for the user to record a "pointing-up" direction for this virtual plane. The function of using the probe motion to interface with the DEX-Ray™ system allows a surgeon to control the DEX-Ray™ system intra-operatively, without the need to touch a physical interface. Because the probe is tracked by a tracking system, when the probe enters a defined area it can be used as an interface. This facilitates controlling the system from where the surgeon or other user is standing, generally near the patient, without having to walk to where the DEX-RAY™ trolley may be located. The probe can be used in conjunction with other non-manual interfaces, such as, for example, a foot switch, as is utilized in DEX-Ray™. FIG. 29 depicts the Vector Recording Page at the beginning of the process, where a user is directed to choose an upper point for the vector, and FIG. 30 depicts an exemplary Vector Recording Page after a vertical vector has been specified by a user, as indicated in the Status Box.

The Vector Recording Page has a number of components, which are next described. Instructions Box (top left of FIGS. 29-30) and Drawing Box (top right of FIGS. 29-30): these boxes visually present instructions to a user while he is recording the vector. A grid in blue, for example, at the bottom of the Drawing Box indicates a horizontal plane. A red line with two red spheres at each end, for example, indicates the vertical vector in space. When a user is trying to record the upper point of the vector, the upper sphere will flash until the recording of the upper point. Then the lower sphere will take over to flash, instructing the user to record the lower point of the vector. Once the recording process finishes, no spheres flash.

Status Box (bottom left): the current running status, i.e., correct or incorrect, will be displayed step by step in this box. If every thing is all right, the scripts are written, for example, in green. Otherwise, they can be, for example, written in red.

Record Points Button (bottom left): a user can, for example, click this button each time he picks each end point of the vector in space, as described above. Test Vector Button (center of buttons trio at bottom left): once the vector recording process finishes, the user may click this button to test a chosen vector, and the interface will then shift to an interface where the user may move the probe and see if the cursor movement is comfortable or not. When the testing finishes, the user can click a return button to return the Vector Recording Page. Vector testing can be skipped if a user is sure that the cursor movement is satisfactory. Clear Vector Button: this button can be used to clear a vector with which a user is unsatisfied. At this point, the user can re-record another vector until he feels comfortable with the cursor movement on the screen associated with the chosen vector.

"Next" Button (bottom right): when the process of vector recording finishes, a user can, for example, click this button to enter the Navigation Page. If a user tries to open the Navigation Page without recording a vector, a warning message can pop up and a default vector can be used for the virtual plane.

FIG. 31 depicts the Navigation Page in Console Mode. The Navigation Page operates in two modes, Navigation/Guidance mode and Console Mode. Navigation/Guidance Mode is essentially illustrated in FIGS. 20-24 above. As opposed to the Navigation/Guidance Mode used for navigating through the patient space, the Console Mode can be used for user interactions. In Navigation/Guidance mode, there are no buttons, menu, sliders, or other user interaction objects (except, for example, a button for snapshot taking), and the combined video and virtual image is displayed in full screen. In Console Mode, on the other hand, items such as buttons, menus, sliders and tabs are available for various user interactions.

The Console Mode interface is grouped into three parts: navigation preview in the upper left corner, tabs panel in the upper right corner and an adjustment and function panel at the bottom. These displays and their associated functionalities are next described.

Navigation preview: preview for navigation. The results of the user interactions accessible via this page are reflected in this window.

Tabs panel: contains two tabs—object tab and preference tab. The object tab is used to select or show/hide graphic objects to be displayed in the navigation window. On the other hand, a user can modify the display preference of the navigation window as desired via the preference tab.

Adjustment and function panel: Contains three sub-areas: transparency adjustment, zoom and detail adjustment, and function buttons array. A user can adjust parameters of both the graphics objects and the live video image and enable/disable couples of navigation functions using this panel.

DEX-Ray allows a user to interact with the system without having to touch an interface. As described above, this is particularly useful in sterile contexts, where it is inconvenient for a medical care professional to get up from where the patient is and go push keys or manipulate a mouse connected to the computer. Thus, DEX-Ray utilizes the probe to move a displayed cursor across the various fields and views in Console Mode of the Navigation Page, and uses a foot switch to indicate a selection. The cursor control and click functions of a mouse are thus mapped to the probe and foot switch, respectively, allowing free handed control of the DEX-Ray system. The probe is moved in a virtual plane, which can, for example, be defined as the horizontal plane to which the vector selected at the Vector Recording Page is normal. Alternatively, any plane within the tracking area can be used as may be convenient. To interact with the Console Mode of the Navigation Page, a user moves the probe within a defined area of space where the plane is located, and thus can move the cursor across the screen. As noted, a particular area of the screen can be selected, for example, by clicking or holding down a foot switch. Other non-manual interactions are possible as may be convenient in a given context, such as, for example, voice control, etc., the desire to free a user's hands form interaction being paramount.

On the Navigation Page, to swap between Navigation/Guidance mode and Console Mode a user can, for example, short-click a foot switch while the cursor is located in the navigation preview. To take screen snapshots, for example, a user can long-click (two seconds) the foot switch while DEX-Ray™ is in navigation/guidance mode; the snapshot files can be stored, for example, in a 'Profile/<CaseName>' folder under the same directory where the DEX-RAY™ executable program is located.

The DEX-Ray example described above is for illustration purposes only, and its functionality while described, is by way of example, and not intended to limit of fix other possible embodiments of the present invention.

It is noted that the present invention is directed to a navigation and guidance system. Inasmuch as the above described procedures are merely exemplary embodiments of the invention, pre-operation planning is understood not to be required. Alternatively, for example, real time imaging methods such as, for example, ultrasound could be used as the source of image data for registration and navigation purposes. Additionally, a surgical plan may be generated using the navigation system itself.

The present invention has been described in connection with exemplary embodiments and implementations, as examples only. It will be understood by those having ordinary skill in the pertinent art that modifications to any of the embodiments or preferred embodiments may be easily made without materially departing from the scope and spirit of the present invention which is defined by the appended claims. Such modifications can include, for example, using real time scan data to display computer generated objects and structures over real time video, or using real time scan data in place of video and mix the real time scan data (such as, for example, ultrasound) with selected pre-operative scan data (such as, for example, CT or MRI).

What is claimed:

1. A system, comprising:
    a probe comprising a housing and a physical pointer having a defined length;
    a video camera provided in the housing;
    a tracking system arranged to track the three-dimensional positions of the video camera and various reference points on a subject;
    a data processor with pre-stored three dimensional subject image data; and
    a display;
    wherein the data processor augments real time images from the video camera with virtual objects generated from the three dimensional subject image data in response to input from the tracking device and displays a composite image on the display; and
    wherein the physical pointer is attached to the housing at a defined offset from the housing so that all or a portion of it can been seen at a defined position within the view of the video camera.

2. The system of claim 1, where the pre-stored patient image data comprises one of one or more three dimensional data sets and multi-modal scan data.

3. The system of claim 1, wherein the housing and the physical pointer can be sterilized.

4. The system of claim 1, wherein a user can input display parameters and other system controls without physically touching an interface of the data processor with his hand.

5. The system of claim 4, wherein a user can interface with the system via at least one of a foot switch and manipulation of the probe in a defined area in space.

6. The system of claim 1, wherein a longitudinal axis of the pointer is substantially parallel to a central longitudinal axis of the housing.

7. The system of claim 1, wherein the pointer protrudes a defined length from the surface of the camera.

8. The system of claim 1, wherein the length of the pointer and its offset from the housing are chosen so as to place a video image of the pointer in a bottom third of the field of view, and at approximately the horizontal center, of an image generated by the camera.

9. An augmented reality visualization system, comprising:
    a probe comprising a housing and a physical pointer having a defined length;
    a video camera provided in the housing;
    a tracking system arranged to track the three-dimensional positions of the probe and various reference points on the visualized object;
    a data processor with pre-stored three dimensional visualized object imaging data; and
    a display;
    wherein the data processor augments real time images from the video camera with virtual objects generated from the three dimensional visualized object imaging data in response to input from the tracking device and displays a composite image on the display; and
    wherein the physical pointer is attached to the housing at a defined offset from the housing so that all or a portion of it can be seen at a defined position within the view of the video camera.

10. The system of claim 9, where the pre-stored visualized object imaging data comprises multi-modal scan data.

11. The system of claim 9, where the pre-stored visualized object imaging data comprises one or more three dimensional data sets.

12. The system of claim 9, wherein the visualized object is a human or other mammal and wherein the visualized object imaging data is the output of one or more medical imaging processes.

13. The system of claim 9, wherein the augmented reality visualization is used in connection with surgical navigation.

14. The system of either of claims 1 or 9, wherein the composite image is a positionally correct fusion of real-time images and virtual images.

15. The system of claim 14, wherein real-time images and virtual images of the same object, objects, or structures have substantially no or minimal overlap.

* * * * *